United States Patent
Hogan

(10) Patent No.: US 7,449,328 B2
(45) Date of Patent: *Nov. 11, 2008

(54) PROBE MATRIX-BASED DEVICE FOR IDENTIFYING MICROORGANISMS

(75) Inventor: James J. Hogan, Coronado, CA (US)

(73) Assignee: Gen-Probe Incorporated, San Diego, CA (US)

( * ) Notice: Subject to any disclaimer, the term of this patent is extended or adjusted under 35 U.S.C. 154(b) by 235 days.

This patent is subject to a terminal disclaimer.

(21) Appl. No.: 10/929,710

(22) Filed: Aug. 30, 2004

(65) Prior Publication Data

US 2005/0026206 A1 Feb. 3, 2005

Related U.S. Application Data

(63) Continuation of application No. 09/565,238, filed on May 3, 2000, now Pat. No. 6,821,770.

(60) Provisional application No. 60/132,411, filed on May 3, 1999, provisional application No. 60/150,149, filed on Aug. 20, 1999.

(51) Int. Cl.
*C07H 21/04* (2006.01)
*C12Q 1/68* (2006.01)

(52) U.S. Cl. ............. 435/287.2; 435/6; 435/91.1; 435/91.2; 536/23.1; 536/24.3; 536/24.31; 536/24.32

(58) Field of Classification Search ............. None
See application file for complete search history.

(56) References Cited

U.S. PATENT DOCUMENTS

| | | | |
|---|---|---|---|
| 4,851,330 A | 7/1989 | Kohne | 435/6 |
| 4,977,251 A | 12/1990 | Saylers et al. | 536/27 |
| 5,030,557 A | 7/1991 | Hogan et al. | 435/6 |
| 5,049,489 A | 9/1991 | Aldrich et al. | 435/6 |
| 5,084,565 A | 1/1992 | Parodos et al. | 536/27 |
| 5,185,439 A | 2/1993 | Arnold, Jr. et al. | 536/24.3 |
| 5,283,174 A | 2/1994 | Arnold, Jr. et al. | 435/6 |
| 5,364,763 A | 11/1994 | Kacian | 435/7.32 |
| 5,374,522 A | 12/1994 | Murphy et al. | 435/6 |
| 5,403,710 A | 4/1995 | Weisburg et al. | 435/6 |
| 5,426,027 A | 6/1995 | Lott et al. | 435/6 |

(Continued)

FOREIGN PATENT DOCUMENTS

EP 0318245 5/1989

(Continued)

OTHER PUBLICATIONS

Regensburger et al. (J. of General Microbiology, vol. 134, pp. 1197-1204, 1988).*

(Continued)

*Primary Examiner*—Jeanine A Goldberg
(74) *Attorney, Agent, or Firm*—Michael J. Gilly

(57) ABSTRACT

Device for identifying microbial organisms using a collection of polynucleotide probes, each probe having binding specificity for the ribosomal nucleic acids of at least one microbe. The collection of probes is organized into a series of "addresses" that provide information about the presence or absence of one or more polynucleotide sequences in the biological sample. The system is particularly suited to automated analysis.

20 Claims, 3 Drawing Sheets

U.S. PATENT DOCUMENTS

| | | | | |
|---|---|---|---|---|
| 5,514,551 A | | 5/1996 | Yang et al. .................. 435/6 |
| 5,539,082 A | | 7/1996 | Nelson et al. ............... 530/300 |
| 5,541,308 A | | 7/1996 | Hogan et al. ............... 536/23.1 |
| 5,552,279 A | | 9/1996 | Weisburg et al. ............... 435/6 |
| 5,580,971 A | | 12/1996 | Mitsuhashi .............. 536/24.32 |
| 5,582,975 A | | 12/1996 | Milliman ....................... 435/6 |
| 5,591,578 A | | 1/1997 | Meade et al. .................... 435/6 |
| 5,593,836 A | | 1/1997 | Niemiec et al. ................ 435/6 |
| 5,601,984 A | | 2/1997 | Kohne ........................... 435/6 |
| 5,620,847 A | | 4/1997 | Greisen et al. .................. 435/6 |
| 5,627,275 A | | 5/1997 | Roll .......................... 536/23.7 |
| 5,631,132 A | | 5/1997 | Lott et al. ....................... 435/6 |
| 5,635,348 A | * | 6/1997 | Leong ........................... 435/6 |
| 5,635,353 A | | 6/1997 | Lott et al. ....................... 435/6 |
| 5,635,367 A | | 6/1997 | Lund ............................ 435/34 |
| 5,645,992 A | | 7/1997 | Lott et al. ....................... 435/6 |
| 5,656,207 A | | 8/1997 | Woodhead et al. ........... 252/700 |
| 5,656,740 A | | 8/1997 | Grosz et al. ................. 536/23.1 |
| 5,674,684 A | | 10/1997 | Hogan et al. .................... 435/6 |
| 5,677,128 A | | 10/1997 | Hogan et al. .................... 435/6 |
| 5,681,698 A | | 10/1997 | Hogan ........................... 435/6 |
| 5,688,644 A | | 11/1997 | Lott et al. ....................... 435/6 |
| 5,705,339 A | | 1/1998 | Nietupski et al. ............... 435/6 |
| 5,708,160 A | | 1/1998 | Goh et al. .................. 536/24.32 |
| 5,714,321 A | | 2/1998 | Hogan ........................... 435/6 |
| 5,756,011 A | | 5/1998 | Woodhead et al. ........... 252/700 |
| 5,770,369 A | | 6/1998 | Meade et al. .................... 435/6 |
| 5,770,373 A | | 6/1998 | Britschgi |
| 5,776,694 A | | 7/1998 | Sheiness et al. ................. 435/6 |
| 5,786,167 A | | 7/1998 | Tuompo et al. ............... 435/34 |
| 5,811,269 A | | 9/1998 | Nadeau et al. ............. 435/91.1 |
| 5,824,518 A | | 10/1998 | Kacian et al. ............ 435/91.21 |
| 5,837,452 A | | 11/1998 | Clark et al. ..................... 435/6 |
| 5,840,488 A | | 11/1998 | Hogan ........................... 435/6 |
| 5,849,488 A | | 12/1998 | Alatossava et al. .............. 435/6 |
| 5,849,497 A | | 12/1998 | Steinman ....................... 435/6 |
| 5,906,917 A | | 5/1999 | Hammond ...................... 435/6 |
| 5,945,286 A | | 8/1999 | Krihak et al. ................... 435/6 |
| 5,952,202 A | | 9/1999 | Aoyagi et al. ............... 435/91.2 |
| 5,994,066 A | | 11/1999 | Bergeron et al. ................ 435/6 |
| 5,998,135 A | | 12/1999 | Rabbani et al. ................. 435/6 |
| 6,001,564 A | | 12/1999 | Bergeron et al. ................ 435/6 |
| 6,025,132 A | | 2/2000 | Jannes et al. .................... 435/6 |
| 6,028,187 A | | 2/2000 | Hogan ...................... 536/24.32 |
| 6,031,091 A | | 2/2000 | Arnold, Jr. et al. ......... 536/25.34 |
| 6,100,030 A | | 8/2000 | McCasky Feazel et al. |
| 6,214,545 B1 | | 4/2001 | Dong et al. |
| 6,252,059 B1 | | 6/2001 | McDonough et al. |
| 6,821,770 B1 | * | 11/2004 | Hogan ..................... 435/287.2 |

FOREIGN PATENT DOCUMENTS

| | | |
|---|---|---|
| EP | 0422872 | 4/1991 |
| EP | 0479117 | 4/1992 |
| EP | 0502271 | 9/1992 |
| EP | 0517361 | 12/1992 |
| EP | 0639649 | 2/1995 |
| EP | 0786519 | 7/1997 |
| EP | 0808907 | 11/1997 |
| JP | 7255486 | 10/1995 |
| WO | 8803937 | 6/1988 |
| WO | 8806189 | 8/1988 |
| WO | 8905359 | 6/1989 |
| WO | 9015157 | 12/1990 |
| WO | 9116454 | 10/1991 |
| WO | 9205280 | 4/1992 |
| WO | 9207096 | 4/1992 |
| WO | 9304201 | 3/1993 |
| WO | 9402636 | 2/1994 |
| WO | WO9419489 | 9/1994 |
| WO | 9428174 | 12/1994 |
| WO | 9600298 | 1/1996 |
| WO | 9619585 | 6/1996 |
| WO | 9621741 | 7/1996 |
| WO | 9622392 | 7/1996 |
| WO | WO9637177 | 11/1996 |
| WO | 9641878 | 12/1996 |
| WO | 9705282 | 2/1997 |
| WO | 9729212 | 8/1997 |
| WO | 9810093 | 3/1998 |
| WO | 9810101 | 3/1998 |
| WO | 9811257 | 3/1998 |
| WO | 9820157 | 5/1998 |
| WO | 9820162 | 5/1998 |
| WO | 9828444 | 7/1998 |
| WO | 9845473 | 10/1998 |
| WO | 9857158 | 12/1998 |
| WO | 9857159 | 12/1998 |
| WO | 9914361 | 3/1999 |
| WO | 9935285 | 7/1999 |
| WO | 9938612 | 8/1999 |
| WO | 9954502 | 10/1999 |
| WO | 9958713 | 11/1999 |
| WO | 0066789 | 11/2000 |

OTHER PUBLICATIONS

Adhern, "Biochemical, Reagent Kits Offer Scientists Good Return On Investment", *The Scientist Library*, 9(15):1-5 (1998).

Arnold, Jr. et al., "Assay Formats Involving Acridinium-Ester-Labeled DNA Probes", *Clin. Chem.*, 35(8):1586-1594 (1989).

Barone et al., "In situ activation of bis-dialkylaminophosphines—a new method for synthesizing deoxyoligonucleotides on polymer supports", *Nuc. Acids Res.*, 12(10):4051-4061 (1984).

Farmer, III, "*Enterobacteriaceae*: Introduction and Identification", *Manual of Clin. Microbiol.*, 6th Ed., P.R. Murray et al., eds., chpt. 32:438-449 (1995).

Griesen et al., "PCR Primers and Probes for the 16S rRNA Gene of Most Species of Pathogenic Bacteria, Including Bacteria Found in Cerebrospinal Fluid", *J. Clin. Microbiol.*, 32(2):335-351.

Kloos et al., "*Staphylococcus* and *Micrococcus*", *Manual of Clin. Microbiol.*, 6th Ed., P.R. Murray et al., eds., chpt. 22:282-298 (1995).

Lane et al., "Rapid determination of 16S ribosomal RNA sequences for phylogenetic analyses", *Proc. Natl. Acad. Sci. USA*, 82:6955-6959 (1985).

Loge et al., "Development of a Fluorescent 15S rRNA Oligonucleotide Probe Specific to the Family *Enterobacteriaceae*", *Water Environment Res.* 71(1):75-83 (1999).

Mabilat et al., "Routine Identification of *Mycobacterium tuberculosis* Complex Isolates by Automated Hybridization", *J. Clin. Microbiol.*, 32(11):2702-2705 (1994).

Sambrook et al., *Molecular Cloning—A Laboratory Manual*, 2nd Ed., vol. 2, Chpt. 9, "Analysis and Cloning of Eukaryotic Genomic DNA"; Chpt. 10, "Preparation of Radiolabeled DNA and RNA Probes"; and Chpt. 11, "Synthetic Oligonucleotide Probes".

Barash et al., "EP786519/*Staphylococcus aureus* contig Seq. ID #5176", Abctract, XP002156295, 1 pg. (Jul. 30, 1997).

Barast et al., "EP786519/*Staphylococcus aureus* contig Seq. ID #3420", Abstract, XP002156296, 1 pg. (Jul. 30, 1997).

Barash et al., EP786519/*Staphylococcus aureus* contig Seq. ID #3419, Abstract, XP002156297, 1 pg. (Jul. 30, 1997).

Derwent Publications Ltd., London, GB, AN 1993-171846, "Oligonucleotide Probe Used For The Detection of Microbes", & JP 05 103700 A (NEC Corp.), Apr. 27, 1993, Abstract XP002156224, 1 pg.

Fuller et al., "Comparison of an rRNA probe matrix to conventional methods for rapid identification of clinically significant bacteria and fungi recovered from blood culture specimens", *Abstracts of the Interscience Conference on Antimicrobial Agents and Chemotherapy*, 39:221 (1999), Abstract, XP002156294, 1 pg.

Gingers et al., "Simultaneous Genotyping and Species Identification Using Hybridization Pattern Recognition Analysis of Generic *Mycobacterium* DNA Arrays", XP-002156298, Cold Spring Harbor Lab. Press, (*Genome Res.*), pp. 435-448 (1998).

Minagawa H., "Oligonucleotide Probe and Detection of Bacterium with the Same", Abstract XP002155681, 1 pg.

Normand et al., "Analysis of the ribosomal RNA operon in the actinomycete Frankia", Gene, 111:119-124 (1992), Abstract XP002155629, 2 pgs.

Troesch et al., "*Mycobacterium* Species Identification and Rifampin Resistance Testing with High-Density DNA Probe Arrays", XP-002130858, *J. Clin. Microbiol.*, 37(1):49-55 (1999).

Van der Giessen, "Comparison of the 23s ribosomal RNA genes and the spacer region between the 16s and the 23s rRNA genes of the closely related *Mycobacterium avium* and *Mycobacterium paratuberculosis* and the fast-growing *Mycobacterium phlei*", Microbiology, 140:1103-1108 (1994), Abstract XP002155679, 1 pg.

Yoshiharu S., "Method for Specifying DNA Base Sequence", Abstract XP002155682, 1 pg.

Facklam et al. "*Streptococci* and *Aerococci*" Manual of Clin. Microbiol., 4th Ed., E.H. Lennette, et al., eds., (M.B. Coyle, et al., Sect. III eds.), Chpt. 16:154-175 (1985).

Barns et al., "Evolutionary Relationships among Pathogenic *Candida* Species and Relatives", *J. Bacteriology*, 173(7):2250-2255 (1991).

Brando, Cell Culture Systems, *Manual of Clin. Microbiol.*, 6th Ed., vol. III, Chpt. 14, pp. 158-165 (1995).

Facklam et al., "Identification of *Enterococcus* Species Isolated form Human Infections by a Conventional Test Scheme", *J. Clin. Microbiol.*, 27(4):731-734 (1989).

Herrmann, "Immunoassays for the Diagnosis of Infectious Diseases", *Manual of Clin. Microbiol.*, 6th Ed., vol. III, Chpt. 11, pp. 110-122 (1995).

Jorgensen et al., "Controlled Clinical Laboratory Comparison of BACTEC Plus Aerobic/F Resin Medium with BacT/Alert Aerobic FAN Medium for Detection of Bacteremia and Fungemia", *J. Clin. Microbiol.*, 35(1):53-58 (1997).

McCabe et al., Bacterial Species Identification After Amplification with a Universal Primer Pair, *Pediatric Res.*, Program Issue APS-SPR, 39(4), Pt. 2, p. 179A, Abstract No. 1059 (1996).

Miller et al., "Substrate Utilization Systems for the Identification of Bacteria and Yeasts", *Manual of Clin. Microbiol.*, 6th Ed., vol. III, Chpt. 10, pp. 103-109 (1995).

Odds et al., "Prevalence of *Candida dubliniensis* Isolates in a Yeast Stock Collection", *J. Clin. Microbiol.*, 36(10):2869-2873 (1998).

Onderdonk et al., "Gas-Liquid and High-Performance Liquid Chromatographic Methods for the Identification of Microorganisms", *Manual of Clin. Microbiol.*, 6th Ed., vol. III, Chpt. 12, pp. 123-129 (1995).

Podzorski et al., "Molecular Detection and Identification of Microorgansims", *Manual of Clin. Microbiol.*, 6th Ed., vol. III, Chpt. 13, pp. 130-157 (1995).

Roller et al., "In situ probing of Gram-positive bacteria with high DNA G+C content using 23S rRNA-targeted oligonucleotides", *Microbiology*, 140:2849-2858 (1994).

Roller et al., Gram-positive bacteria with a high DNA G+C content are characterized by a common insertion within their 23S rRNA genes, *J. Gen. Microbiol.*, 138:1167-1175 (1992).

Service, "Microchip Arrays Put DNA on the Spot", *Science*, 282:396-399 (1998).

Sullivan et al., "*Candida dubliniensis* sp. nov.:phenoytpic and molecular characterization of a novel species associated with oral candidosis in HIV-infected individuals", *Microbiology*, 141:1507-1521 (1995).

Sullivan et al., "*Candida dubliniensis*: An Emerging Opportunistic Pathogen", *Curr. Topics in Med. Mycology*, 8(1-2):15-25 (1997).

Voordouw, "Reverse Sample Genome Probing of Microbial Community Dynamics", *ASM News*, 64(11):627-633 (1998).

Wilson (Guest Editor), "Blood Cultures", *Clin. in Lab. Med.*, 14(1):1-4 (1994).

Anthony et al., "Rapid Diagnosis of Bacteremia by Universal Amplification of 23S Ribosomal DNA Followed by Hybridization to an Oligonucleotide Array", *J. Clin. Microbiol.*, 38(2):781-788 (2000).

Daly et al., "Use of Rapid, Nonradioactive DNA Probes in Culture Confirmation Test To Detect *Streptococcus agalactiae, Haemophilus influenzae*, and *Enterococcus* spp. From Pediatric Patients with Significant Infections", *J. Clin. Microbiol.*, 29(1):80-82 (1991).

Davis et al., "Direct Identification of Bacterial Isolates in Blood Cultures by Using a DNA Probe", *J. Clin. Microbiol.*, 29(10):2193-2196 (1991).

Dunne et al., "Blood Cultures III", *Cumitech*, vol. 1B:, pp. 1-21 (1997).

Freney et al., Description and Evaluation of the Semiautomated 4-Hour Rapid ID 32 Strep Method for Identification of *Streptococci* and Members of Related Genera, *J. Clin. Microbiol.*, 30(10):2657-2661 (1992).

Jansen et al., "Rapid Identification of Bacteria in Blood Cultures by Using Fluorescently Labeled Oligonucleotide Probes", *J. Clin. Microbiol.*, 38(2):814-817 (2000).

Kempf et al., "Fluorescent In Situ Hybridization Allows Rapid Identification of Microorganisms in Blood Cultures", *J. Clin. Microbiol.*, 38(2):830-838 (2000).

Lim et al., "Genotypic Identification of Pathogenic *Mycobacterium* Species by Using a Nonradioactive Oligonucleotide Probe", *J. Clin. Microbiol.*, 29(6):1276-1278 (1991).

McCabe et al., "Amplification of Bacterial DNA Using Highly Conserved Sequences: Automated Analysis and Potential for Molecular Triage of Sepsis", *Pediatrics*, 95(2):165-169 (1995).

Turenne et al., "Rapid Identification of Bacteria from Positive Blood Cultures by Fluorescence-Based PCR-Single-Strand Conformation Polymorphism Analysis of the 16S rRNA Gene", *J. Clin. Microbiol.*, 38(2):513-520 (2000).

Weinstein et al., "The Clinical Significance of Positive Blood Cultures in the 1990s" A Prospective Comprehensive Evaluation of the Microbiology, Epidemiology and Outcome of Bacteremia and Fungemia in Adults, *Clin. Infect. Diseases*, 24:584-602 (1997).

Weinstein et al., "Current Blood Culture Methods and Systems: Clinical Concepts. Technology and Interpretation of Results", *Clin. Infect. Diseases*, 23:40-46 (1996).

Weinstein et al., "Controlled Evaluation of BACTEC Plus 26 and Roche Septi-Chek Aerobic Blood Culture Bottles", *J. Clin. Microbiol.*, 29(5):879-882 (1991).

Matthews et al., "Analytical strategies for the use of DNA probes," Analytical Biochemistry, PMID 3285726, Feb. 1998, 169(1):1-25, Academic Press/Elsevier. Orlando, FL, USA.

Regensburger et al., "DNA probes with different specificities from a cloned 23S rRNA gene of *Micrococcus luteus*," Journal of General Microbiology, 1998, 134:1197-1204, Society for General Microbiology, Reading, UK.

\* cited by examiner

SEQUENCE LISTING

```
<160> NUMBER OF SEQ ID NOS: 61

<210> SEQ ID NO 1
<211> LENGTH: 16
<212> TYPE: DNA
<213> ORGANISM: pan-bacterial

<400> SEQUENCE: 1
cgacaaggaa tttcgc                                                      16

<210> SEQ ID NO 2
<211> LENGTH: 17
<212> TYPE: DNA
<213> ORGANISM: pan-bacterial

<400> SEQUENCE: 2
taccttagga ccgttat                                                     17

<210> SEQ ID NO 3
<211> LENGTH: 16
<212> TYPE: DNA
<213> ORGANISM: pan-bacterial

<400> SEQUENCE: 3
caggtcggaa cttacc                                                      16

<210> SEQ ID NO 4
<211> LENGTH: 22
<212> TYPE: DNA
<213> ORGANISM: pan-fungal
```

```
<400> SEQUENCE: 4
gtctggacct ggtgagtttc cc                                            22

<210> SEQ ID NO 5
<211> LENGTH: 23
<212> TYPE: DNA
<213> ORGANISM: pan-fungal

<400> SEQUENCE: 5
cgtgttgagt caaattaagc cgc                                           23

<210> SEQ ID NO 6
<211> LENGTH: 26
<212> TYPE: DNA
<213> ORGANISM: pan-fungal

<400> SEQUENCE: 6
gctctcaatc tgtcaatcct tattgt                                        26

<210> SEQ ID NO 7
<211> LENGTH: 18
<212> TYPE: DNA
<213> ORGANISM: Gram(+) bacteria

<400> SEQUENCE: 7
gagggaacct ttgggcgc                                                 18

<210> SEQ ID NO 8
<211> LENGTH: 29
<212> TYPE: DNA
<213> ORGANISM: Gram(+) bacteria

<400> SEQUENCE: 8
ctccgttacc ttttaggagg cgaccgccc                                     29

<210> SEQ ID NO 9
<211> LENGTH: 21
<212> TYPE: DNA
<213> ORGANISM: Gram(+) bacteria

<400> SEQUENCE: 9
ctccgttaca ttttaggagg c                                             21

<210> SEQ ID NO 10
<211> LENGTH: 29
<212> TYPE: DNA
<213> ORGANISM: Actinomycetes [High (G+C)] bacteria

<400> SEQUENCE: 10
cgagcatctt tactcgtagt gcaatttcg                                     29

<210> SEQ ID NO 11
<211> LENGTH: 25
<212> TYPE: DNA
<213> ORGANISM: Actinomycetes [High (G+C)] bacteria

<400> SEQUENCE: 11
ccgagtctgt ggttgagaca gtggg                                         25

<210> SEQ ID NO 12
<211> LENGTH: 25
<212> TYPE: DNA
```

<213> ORGANISM: Actinomycetes [High (G+C)] bacteria

<400> SEQUENCE: 12
ggtctttccg tcctgccgcg cgtaa                                      25

<210> SEQ ID NO 13
<211> LENGTH: 17
<212> TYPE: DNA
<213> ORGANISM: Enterobacteriaceae

<400> SEQUENCE: 13
ccgcttgctc tcgcgag                                               17

<210> SEQ ID NO 14
<211> LENGTH: 41
<212> TYPE: DNA
<213> ORGANISM: Enterobacteriaceae

<400> SEQUENCE: 14
gtcgcttctc tttgtatgcg ccattgtagc acgtgtgtag c                    41

<210> SEQ ID NO 15
<211> LENGTH: 24
<212> TYPE: DNA
<213> ORGANISM: Enterobacteriaceae

<400> SEQUENCE: 15
ggactacgac gcactttatg aggt                                       24

<210> SEQ ID NO 16
<211> LENGTH: 24
<212> TYPE: DNA
<213> ORGANISM: Enterococcus

<400> SEQUENCE: 16
ctcctaggtg ccagtcaaat tttg                                       24

<210> SEQ ID NO 17
<211> LENGTH: 31
<212> TYPE: DNA
<213> ORGANISM: Enterococcus

<400> SEQUENCE: 17
tctacggggc ttttacccctt tctagcagac c                              31

<210> SEQ ID NO 18
<211> LENGTH: 26
<212> TYPE: DNA
<213> ORGANISM: Enterococcus

<400> SEQUENCE: 18
cctcgtgttc cgccgtactc aggatc                                     26

<210> SEQ ID NO 19
<211> LENGTH: 21
<212> TYPE: DNA
<213> ORGANISM: Enterococcus

<400> SEQUENCE: 19
catcattctc aattccgagg c                                          21

<210> SEQ ID NO 20
<211> LENGTH: 38

```
<212> TYPE: DNA
<213> ORGANISM: Enterococcus

<400> SEQUENCE: 20
tagccctaaa gctatttcgg agagaaccag ctatctcc                                 38

<210> SEQ ID NO 21
<211> LENGTH: 26
<212> TYPE: DNA
<213> ORGANISM: Enterococcus

<400> SEQUENCE: 21
ccctagtcca aacagtgctc tacctc                                              26

<210> SEQ ID NO 22
<211> LENGTH: 30
<212> TYPE: DNA
<213> ORGANISM: Staphylococcus genus

<400> SEQUENCE: 22
ccgaactgag aacaacttta tgggatttgc                                          30

<210> SEQ ID NO 23
<211> LENGTH: 17
<212> TYPE: DNA
<213> ORGANISM: Staphylococcus genus

<400> SEQUENCE: 23
ttgacctcgc ggtttcg                                                        17

<210> SEQ ID NO 24
<211> LENGTH: 39
<212> TYPE: DNA
<213> ORGANISM: Staphylococcus genus

<400> SEQUENCE: 24
gcgattccag cttcatgtag tcgagttgca gactacaat                                39

<210> SEQ ID NO 25
<211> LENGTH: 24
<212> TYPE: DNA
<213> ORGANISM: Campylobacter spp

<400> SEQUENCE: 25
ggttcttagg atatcaagcc cagg                                                24

<210> SEQ ID NO 26
<211> LENGTH: 39
<212> TYPE: DNA
<213> ORGANISM: Campylobacter spp

<400> SEQUENCE: 26
gtctctaagt tctagcaagc tagcaccctc atatctcta                                39

<210> SEQ ID NO 27
<211> LENGTH: 29
<212> TYPE: DNA
<213> ORGANISM: E. coli

<400> SEQUENCE: 27
gggtaacgtc aatgagcaaa ggtattaac                                           29

<210> SEQ ID NO 28
```

```
<210> SEQ ID NO 28
<211> LENGTH: 40
<212> TYPE: DNA
<213> ORGANISM: E. coli

<400> SEQUENCE: 28
tttactccct cctccccgc tgaaagtact ttacaacccg                              40

<210> SEQ ID NO 29
<211> LENGTH: 27
<212> TYPE: DNA
<213> ORGANISM: E. coli

<400> SEQUENCE: 29
cacggagtta gccggtgctt cttctgc                                            27

<210> SEQ ID NO 30
<211> LENGTH: 22
<212> TYPE: DNA
<213> ORGANISM: Streptococcus pneumoniae

<400> SEQUENCE: 30
caaagcctac tatggttaag cc                                                 22

<210> SEQ ID NO 31
<211> LENGTH: 37
<212> TYPE: DNA
<213> ORGANISM: Streptococcus pneumoniae

<400> SEQUENCE: 31
acagccttta acttcagact tatctaaccg cctgcgc                                 37

<210> SEQ ID NO 32
<211> LENGTH: 32
<212> TYPE: DNA
<213> ORGANISM: Streptococcus pneumoniae

<400> SEQUENCE: 32
tctcccctct tgcactcaag ttaaacagtt tc                                      32

<210> SEQ ID NO 33
<211> LENGTH: 21
<212> TYPE: DNA
<213> ORGANISM: Pseudomonas aeruginosa

<400> SEQUENCE: 33
cccagagtga tacatgaggc g                                                  21

<210> SEQ ID NO 34
<211> LENGTH: 26
<212> TYPE: DNA
<213> ORGANISM: Pseudomonas aeruginosa

<400> SEQUENCE: 34
ccctagccga aacagttgct ctaccc                                             26

<210> SEQ ID NO 35
<211> LENGTH: 36
<212> TYPE: DNA
<213> ORGANISM: Pseudomonas aeruginosa

<400> SEQUENCE: 35
ctacctaaat agctttcgag gagaaccagc tatctc                                  36
```

```
<210> SEQ ID NO 36
<211> LENGTH: 23
<212> TYPE: DNA
<213> ORGANISM: Candida albicans

<400> SEQUENCE: 36
gctggcctga aaatcaagc acg                                              23

<210> SEQ ID NO 37
<211> LENGTH: 40
<212> TYPE: DNA
<213> ORGANISM: Candida albicans

<400> SEQUENCE: 37
ttgaaacgga gcttccccat ctcttaggat cgactaaccc                           40

<210> SEQ ID NO 38
<211> LENGTH: 37
<212> TYPE: DNA
<213> ORGANISM: Candida albicans

<400> SEQUENCE: 38
ccaagttccg gaattttaac cggattccct ttcgatg                              37

<210> SEQ ID NO 39
<211> LENGTH: 30
<212> TYPE: DNA
<213> ORGANISM: Staphylococcus aureus

<400> SEQUENCE: 39
ccactcaaga gagacaacat tttcgactac                                      30

<210> SEQ ID NO 40
<211> LENGTH: 33
<212> TYPE: DNA
<213> ORGANISM: Staphylococcus aureus

<400> SEQUENCE: 40
gatgattcgt ctaatgtcga cctttgtaac tcc                                  33

<210> SEQ ID NO 41
<211> LENGTH: 32
<212> TYPE: DNA
<213> ORGANISM: Staphylococcus aureus

<400> SEQUENCE: 41
cggaatttca cgtgctccgt cgtactcagg at                                   32

<210> SEQ ID NO 42
<211> LENGTH: 23
<212> TYPE: DNA
<213> ORGANISM: TB Complex

<400> SEQUENCE: 42
ggtagcgctg agacatatcc tcc                                             23

<210> SEQ ID NO 43
<211> LENGTH: 38
<212> TYPE: DNA
<213> ORGANISM: TB Complex

<400> SEQUENCE: 43
ccgctaacca cgacactttc tgtactgcct ctcagccg                             38
```

```
<210> SEQ ID NO 44
<211> LENGTH: 36
<212> TYPE: DNA
<213> ORGANISM: TB Complex

<400> SEQUENCE: 44
cacaaccccg cacacacaac ccctacccgg ttaccc                            36

<210> SEQ ID NO 45
<211> LENGTH: 21
<212> TYPE: DNA
<213> ORGANISM: TB Complex

<400> SEQUENCE: 45
cagaactcca caccccgaa g                                             21

<210> SEQ ID NO 46
<211> LENGTH: 45
<212> TYPE: DNA
<213> ORGANISM: TB Complex

<400> SEQUENCE: 46
tgattcgtca cgggcgccca cacgggta cgggaatatc aaccc                    45

<210> SEQ ID NO 47
<211> LENGTH: 30
<212> TYPE: DNA
<213> ORGANISM: TB Complex

<400> SEQUENCE: 47
ctactaccag ccgaagttcc cacgcagccc                                   30

<210> SEQ ID NO 48
<211> LENGTH: 37
<212> TYPE: DNA
<213> ORGANISM: TB Complex

<400> SEQUENCE: 48
ggagttgatc gatccggttt tgggtggtta gtaccgc                           37

<210> SEQ ID NO 49
<211> LENGTH: 43
<212> TYPE: DNA
<213> ORGANISM: TB Complex

<400> SEQUENCE: 49
ggggtacggg ccgtgtgtgt gctcgctaga ggcttttctt ggc                    43

<210> SEQ ID NO 50
<211> LENGTH: 28
<212> TYPE: DNA
<213> ORGANISM: Listeria monocytogenes

<400> SEQUENCE: 50
ctgagaatag ttttatggga ttagctcc                                     28

<210> SEQ ID NO 51
<211> LENGTH: 25
<212> TYPE: DNA
<213> ORGANISM: Listeria monocytogenes

<400> SEQUENCE: 51
ggcgagttgc agcctacaat ccgaa                                        25
```

```
<210> SEQ ID NO 52
<211> LENGTH: 23
<212> TYPE: DNA
<213> ORGANISM: Candida albicans

<400> SEQUENCE: 52
cggccataaa gacctaccaa gcg                                              23

<210> SEQ ID NO 53
<211> LENGTH: 34
<212> TYPE: DNA
<213> ORGANISM: Candida albicans

<400> SEQUENCE: 53
ccagttctaa gttgatcgtt aaacgtgccc cgga                                  34

<210> SEQ ID NO 54
<211> LENGTH: 34
<212> TYPE: DNA
<213> ORGANISM: Candida albicans

<400> SEQUENCE: 54
tgtctacagc agcatccacc agcagtccgt cgtg                                  34

<210> SEQ ID NO 55
<211> LENGTH: 29
<212> TYPE: DNA
<213> ORGANISM: Candida spp

<400> SEQUENCE: 55
gcgtcaataa aagaacaaca accgatccc                                        29

<210> SEQ ID NO 56
<211> LENGTH: 26
<212> TYPE: DNA
<213> ORGANISM: Candida spp

<400> SEQUENCE: 56
tagtcggcat agtttatggt taagac                                           26

<210> SEQ ID NO 57
<211> LENGTH: 41
<212> TYPE: DNA
<213> ORGANISM: Candida spp

<400> SEQUENCE: 57
cccagaaccc aaagactttg atttctcgta aggtgccgat t                          41

<210> SEQ ID NO 58
<211> LENGTH: 35
<212> TYPE: DNA
<213> ORGANISM: pan-bacterial

<400> SEQUENCE: 58
ggaacttacc cgacaaggaa tttcgctacc ttagg                                 35

<210> SEQ ID NO 59
<211> LENGTH: 36
<212> TYPE: DNA
<213> ORGANISM: pan-bacterial

<400> SEQUENCE: 59
```

-continued

```
accgttatag ttacggccgc cgtttaccgg ggcttc                                36

<210> SEQ ID NO 60
<211> LENGTH: 32
<212> TYPE: DNA
<213> ORGANISM: pan-bacterial

<400> SEQUENCE: 60
gcctggccat cattacgcca ttcgtgcagg tc                                    32

<210> SEQ ID NO 61
<211> LENGTH: 30
<212> TYPE: DNA
<213> ORGANISM: pan-bacterial

<400> SEQUENCE: 61
gcccaaatcg ttacgccttt cgtgcgggtc                                       30
```

PROBE MATRIX-BASED DEVICE FOR IDENTIFYING MICROORGANISMS

RELATED APPLICATIONS

This application is a continuation of application Ser. No. 09/565,238, filed May 3, 2000, now U.S. Pat. No. 6,821,770, issued Nov. 23, 2004, which claims the benefit of U.S. Provisional Application No. 60/132,411, filed May 3, 1999, and U.S. Provisional Application No. 60/150,149, filed Aug. 20, 1999. The disclosures of these related applications are hereby incorporated by reference.

FIELD OF THE INVENTION

The present invention relates to devices for identifying microorganisms. More specifically, the invention relates to the use of a matrix of polynucleotide probes having specificity for ribosomal nucleic acids (rRNA and rDNA) that distinguish species or groups of organisms from each other.

BACKGROUND OF THE INVENTION

The procedures for detecting and identifying infectious organisms are some of the most critical tasks performed in the clinical laboratory. Whereas laboratory diagnoses of infectious diseases formerly were made by experienced technicians using visual inspection of stained clinical material, more rapid and objective results are obtainable using modern techniques. Immunoassays, including radioimmunoassays, enzyme-linked immunoassays, and latex agglutination and immunoblotting assays have developed into powerful diagnostic tools having utilities that are enhanced by the availability of monoclonal antibodies. More recent advances in signal and target amplification have introduced the era of molecular diagnostics based on the use of polynucleotide probes.

Indeed, clinical microbiologists now use an extensive array of techniques for identifying infectious organisms (see *Manual of Clinical Microbiology* Murray et al., eds., 6$^{th}$ edition, ASM Press (1995)). Automated substrate utilization systems typically rely on enzymatic reactions that release chromogenic of fluorogenic compounds, tetrazolium-based indicators of metabolic activity in the presence of different carbon sources, or detection of the acid products of metabolism. The patterns of positive and negative reactions with these substrates establish a biochemical profile that can be used to identify microorganisms isolated from clinical samples. The chromatographic profiles of the more than 300 fatty acids that contribute to the formation of lipids in bacteria and yeast have also been used to phenotype microorganisms. Despite the availability of these very powerful techniques, polynucleotide-based assays are rapidly gaining popularity in clinical laboratory practice.

The specificity of polynucleotide hybridization reactions, together with the extraordinary sensitivity afforded by nucleic acid amplification techniques, has made molecular diagnostics the method of choice for detecting and identifying microbes that are available in only very small quantities. Commonly used DNA probe hybridization formats include: solid phase hybridization, solution-phase hybridization and in situ hybridization. In solid phase hybridization methods, a sample containing microbial polynucleotides is immobilized to a solid support, denatured and then probed with a polynucleotide probe that harbors a detectable label. Unhybridized probe is removed from the system and specifically hybridized probe detected, for example by autoradiography or direct visual observation. In solution-phase hybridization procedures, the target polynucleotide and the labeled probe are free to interact in an aqueous hybridization buffer. Specifically hybridized probe is then detected as an indicator of the presence of target polynucleotides in the mixture. In situ hybridization using formalin-fixed tissue sections is used for obtaining information about the physical distribution and abundance of microorganisms. As they are conventionally practiced, molecular diagnostic assays are conducted to determine whether a particular species or group of organisms is present in a biological sample undergoing testing.

Bacteremia and fungemia are conditions marked by the presence of bacterial and fungal organisms in circulating blood. Sepsis refers to a severe bacterial infection that spreads in the blood throughout the entire body. In septicemia, the presence of microorganisms in the blood indicates that the host's immune system has failed to localize an infection. Organisms responsible for these conditions typically are identified after inoculating a "blood culture bottle" with a sample of patient blood, and then typing any microorganisms that are propagated. Mortality associated with bloodstream infections ranges from an estimated 20% to 50% (see *Clinics in Laboratory Medicine* 14:9 (1994)). An estimated 50,000 deaths each year in the United States result from sepsis (*Vanderbilt Univ. Med. Center Reporter* 1991 Mar. 1; 2(8):1, 3). Thus, substantial attention has been devoted to the diagnosis and treatment of this syndrome.

Unfortunately, the blood culture methods that represent the "gold standard" for diagnosing septicemia have significant limitations (Weinstein, *Clin Infect Dis* 23:40 (1996)). Indeed, no single medium is ideal for propagating all potential bloodstream organisms, some relevant microorganisms grow poorly in conventional media and systems, and positive results require hours to days of incubation. Each of these areas calls for improvement if diagnosis of septicemia is to become more rapid and accurate.

Molecular diagnostic methods employing collections of species-specific DNA probes have been used to identify microorganisms in blood cultures. According to one procedure, microorganisms present in growth-positive culture bottles were first isolated and then Gram-stained and analyzed for morphology (Davis et al., *J. Clin Microbiol.* 29:2193 (1991)). The appearance of the stained organisms determined which of several different polynucleotide probes were employed in a subsequent testing step. Instances wherein positive hybridization results were obtained yielded presumptive identifications. Identification of bacteria that yielded negative hybridization results were limited to observations made after Gram-staining and microscopic analysis. These investigations confirmed that DNA probes could be used for the rapid identification of bacteria taken directly from blood culture bottles, but still required evaluation of Gram-stained microorganisms by an experienced microbiologist. Importantly, polymicrobial bacteremias could not be analyzed in the procedure due to the lack of available probes.

In a study of several hundred positive blood cultures obtained from septicemia patients, Weinstein et al., in *Clin Infect Dis* 24:584 (1997) concluded that the five most common pathogens were *Staphylococcus aureus, Escherichia coli*, coagulase-negative staphylococci, *Klebsiella pneumoniae*, and *Enterococcus* species. Yeasts were also common isolates from blood culture bottles and represented true fungemia when detected about 92% of the time. *Candida albicans* ranked among the top 10 microorganisms causing septicemia. Interestingly, about 91% of the instances of bacteremia and fungemia were unimicrobial while the remaining cases were associated with two or three organisms. The lowest associated mortality among the patients having positive blood cultures were associated with coagulase-negative staphylococci (5.5%) and the highest with yeasts and fungi (35.8%). Most important, septicemia-associated mortality was shown to increase in proportion to the duration of inappropriate antimicrobial therapy. This finding highlighted the importance of an early and proper clinical diagnosis.

The invention detailed below provides a rapid means for identifying microorganisms using techniques that are suited for automated analysis. The invented devices and methods can even be used to resolve the identity of microorganisms that are contained in a mixed population of microorganisms.

SUMMARY OF THE INVENTION

One aspect of the present invention relates to a device for hybridizing nucleic acids. The invented device includes a solid support and a plurality of addresses disposed on the solid support. Each of the addresses includes at least one probe that hybridizes ribosomal nucleic acids from at least one microbial species under high stringency hybridization conditions. The plurality of addresses includes a higher-order address, an intermediate-order address, and a lower-order address. The lower-order address hybridizes ribosomal nucleic acids from a subset of organisms having ribosomal nucleic acids that hybridize at the intermediate-order address. The intermediate-order address hybridizes ribosomal nucleic acids from a subset of organisms having ribosomal nucleic acids that hybridize at the higher-order address. In certain embodiments the solid support of the device is either multi-well plate or a plurality of individual tubes that are maintained in a spaced-apart configuration. In certain preferred embodiments the higher-order address is a pan-bacterial address that specifically hybridizes ribosomal nucleic acids from a plurality of species of Gram$^{(+)}$ bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*. In alternative embodiments the higher-order address is a pan-fungal address that specifically hybridizes ribosomal nucleic acids from a plurality of fungal species. Certain embodiments of the invented device include both a pan-bacterial address as the higher-order address, and a pan-fungal address. The higher-order address can also be a Gram$^{(+)}$ address that specifically hybridizes ribosomal nucleic acids from a plurality of species of Gram$^{(+)}$ bacteria. When the higher-order address is a pan-bacterial address, and regardless of whether or not there is included an address for detecting pan-fungal organisms, the intermediate-order address may be a Gram$^{(+)}$ address that specifically hybridizes ribosomal nucleic acids of a plurality of Gram$^{(+)}$ bacteria, a family Enterobacteriaceae address that specifically hybridizes ribosomal nucleic acids from a plurality of bacteria in the family Enterobacteriaceae, a *Staphylococcus* genus address that specifically hybridizes ribosomal nucleic acids from a plurality of species in the *Staphylococcus* genus, a genus *Enterococcus* address that specifically hybridizes ribosomal nucleic acids from a plurality of species in the genus *Enterococcus* or a *Campylobacter* address that specifically hybridizes ribosomal nucleic acids from a plurality of *Campylobacter* species. In a preferred embodiment the intermediate-order address is the Gram$^{(+)}$ address and the lower-order address is an Actinomycetes address that specifically hybridizes ribosomal nucleic acids of a plurality of bacteria belonging to the High (G+C) subset of Gram$^{(+)}$ bacteria. In another preferred embodiment the intermediate-order address is the Gram$^{(+)}$ address and the lower-order address is an address that specifically hybridizes ribosomal nucleic acids from a plurality of *Mycobacterium* species. For example, the plurality of *Mycobacterium* species may include *Mycobacterium tuberculosis, Mycobacterium bovis, Mycobacterium bovis* BCG and *Mycobacterium africanum*. In still another preferred embodiment when the higher-order address is a pan-bacterial address, and regardless of whether or not there is included an address for detecting pan-fungal organisms, the intermediate-order address is the Gram$^{(+)}$ address and the lower-order address is an address that specifically hybridizes ribosomal nucleic acids of *Streptococcus pneumoniae*. In yet another preferred embodiment when the higher-order address is a pan-bacterial address, and regardless of whether or not there is included an address for detecting pan-fungal organisms, the intermediate-order address is the Gram$^{(+)}$ address and the lower-order address is an address that specifically hybridizes ribosomal nucleic acids from *Listeria monocytogenes*. In still yet another preferred embodiment of the invention when the higher-order address is a pan-bacterial address, and regardless of whether or not there is included an address for detecting pan-fungal organisms, the intermediate-order address is the Gram$^{(+)}$ address, and the lower-order address is an address that specifically hybridizes ribosomal nucleic acids of *Staphylococcus aureus*. A different device according to the invention includes a pan-bacterial address as the higher-order address and, regardless of whether or not there is included an address for detecting pan-fungal organisms, the intermediate-order address is the family Enterobacteriaceae address and the lower-order address is an *E. coli* address that specifically hybridizes ribosomal nucleic acids of *E. coli*. In another preferred embodiment when the higher-order address is a pan-bacterial address, and regardless of whether or not there is included an address for detecting pan-fungal organisms, the lower-order address is a *Staphylococcus aureus* address that specifically hybridizes ribosomal nucleic acids from *Staphylococcus aureus*. In another preferred embodiment when the higher-order address is a pan-bacterial address, and regardless of whether or not there is included an address for detecting pan-fungal organisms, the intermediate-order address is the genus *Enterococcus* address. In another preferred embodiment when the higher-order address is a pan-bacterial address, and regardless of whether or not there is included an address for detecting pan-fungal organisms, the intermediate-order address is the *Campylobacter* address. In other preferred devices the higher-order address is the Gram$^{(+)}$ address and the lower-order address is an address that detects ribosomal nucleic acids from *Mycobacterium tuberculosis, Mycobacterium bovis, Mycobacterium bovis* BCG and *Mycobacterium africanum*. In still other devices the higher-order address is a pan-fungal address, the intermediate-order address specifically hybridizes ribosomal nucleic acids from a plurality of *Candida* species including *Candida albicans, Candida tropicalis, Candida dubliniensis, Candida viswanathii* and *Candida parapsilosis* and the lower-order address specifically hybridizes ribosomal nucleic acids from *Candida albicans* and *Candida dubliniensis* but not *Candida tropicalis, Candida viswanathii* or *Candida parapsilosis*. In another preferred embodiment when the higher-order address is a pan-bacterial address, there is included a pan-fungal address that hybridizes ribosomal nucleic acids from a plurality of fungal species. In a highly preferred embodiment the device includes a pan-fungal address, a pan-bacterial address, a Gram$^{(+)}$ address and an Actinomycetes address. An even more highly preferred device includes a pan-fungal address, a pan-bacterial address, a Gram$^{(+)}$ address, an Actinomycetes address and an addresses that hybridizes ribosomal nucleic acids from bacteria in the family Enterobacteriaceae. An alternative highly preferred device includes a pan-fungal address, a pan-bacterial address, a Gram$^{(+)}$ address, an Actinomycetes address and an addresses that hybridizes ribosomal nucleic acids from *Enterococcus* bacteria. In devices having a pan-fungal address, a pan-bacterial address, a Gram $^{(+)}$ address, an Actinomycetes address and an addresses that hybridizes ribosomal nucleic acids from bacteria in the family Enterobacteriaceae, there can be further included an address that hybridizes ribosomal nucleic acids from *Enterococcus* bacteria. Yet another highly preferred device includes a pan-fungal address, a pan-bacterial address, a Gram$^{(+)}$ address, an Actinomycetes address and a single address that hybridizes ribosomal nucleic acids of *Enterococcus* bacteria and ribosomal nucleic acids from bacteria in the family Enterobacteriaceae. Yet another highly preferred device includes a pan-fungal address, a pan-bacterial address, a Gram$^{(+)}$ address, an Actinomycetes address and an address that hybridizes ribosomal nucleic acids from bacteria in the *Staphylococcus* genus. Yet another highly preferred device includes a pan-fungal address, a pan-bacterial address, a Gram$^{(+)}$ address, an Actinomycetes address and an address that hybridizes ribosomal nucleic acids from a plurality of bacteria in the genus *Campylobacter*. Yet another highly preferred device includes a pan-fungal address, a pan-bacterial address, a Gram$^{(+)}$ address, an Actinomycetes address, an address that hybridizes ribosomal nucleic acids from bacteria in the *Staphylococcus* genus, and an address that hybridizes ribosomal nucleic acids from a plurality of bacteria in the genus *Campylobacter*. Yet another highly preferred device includes a pan-fungal address, a pan-bacterial address, a Gram$^{(+)}$ address, an Actinomycetes address, an address that hybridizes ribosomal nucleic acids from bacteria in the family Enterobacteriaceae, an address that hybridizes ribosomal nucleic acids of *Enterococcus* bacteria, and further includes an address that hybridizes ribosomal nucleic acids from bacteria in the *Staphylococcus* genus and an address that hybridizes ribosomal nucleic acids from a plurality of bacteria in the genus *Campylobacter*. Yet another highly preferred device includes a pan-fungal address, a pan-bacterial address, a Gram$^{(+)}$ address, an Actinomycetes address and a single address that hybridizes ribosomal nucleic acids of *Enterococcus* bacteria and ribosomal nucleic acids from bacteria in the family Enterobacteriaceae, as well as a single address that hybridizes ribosomal nucleic acids from bacteria in the *Staphylococcus* genus and ribosomal nucleic acids from a plurality of bacteria in the genus *Campylobacter*. Yet another highly preferred device includes a pan-fungal address, a pan-bacterial address, a Gram$^{(+)}$ address, an Actinomycetes address, an address that hybridizes ribosomal nucleic acids from bacteria in the family Enterobacteriaceae, an address that hybridizes ribosomal nucleic acids of *Enterococcus* bacteria, and further includes an address that hybridizes ribosomal nucleic acids from bacteria in the *Staphylococcus* genus and an address that hybridizes ribosomal nucleic acids from a plurality of bacteria in the genus *Campylobacter*, and further includes at least one address that specifically hybridizes ribosomal nucleic acids from a single microorganism species. In a highly preferred embodiment the single microorganism species is selected from the group consisting of *Escherichia coli, Streptococcus pneumoniae, Pseudomonas aeruginosa, Candida albicans* and *Staphylococcus aureus*. Yet another highly preferred device includes a pan-fungal address, a pan-bacterial address, a Gram$^{(+)}$ address, an Actinomycetes address, and a single address that hybridizes ribosomal nucleic acids of *Enterococcus* bacteria and ribosomal nucleic acids from bacteria in the family Enterobacteriaceae, as well as a single address that hybridizes ribosomal nucleic acids from bacteria in the *Staphylococcus* genus and ribosomal nucleic acids from a plurality of bacteria in the genus *Campylobacter*, as well as a plurality of addresses that individually hybridize ribosomal nucleic acids from a plurality of microorganism species. Yet another highly preferred device includes a pan-fungal address, a pan-bacterial address, a Gram$^{(+)}$ address and an Actinomycetes address, wherein the pan-bacterial address includes a polynucleotide probe having a sequence selected from the group consisting of SEQ ID NO:1 and SEQ ID NO:58. Yet another highly preferred device includes a pan-fungal address, a pan-bacterial address, a Gram$^{(+)}$ address and an Actinomycetes address, wherein the pan-fungal address comprises a polynucleotide probe having the sequence of SEQ ID NO:4. Yet another highly preferred device includes a pan-fungal address, a pan-bacterial address, a Gram$^{(+)}$ address and an Actinomycetes address, wherein the Gram$^{(+)}$ address includes a polynucleotide probe having the sequence of SEQ ID NO:7. Yet another highly preferred device includes a pan-fungal address, a pan-bacterial address, a Gram$^{(+)}$ address and an Actinomycetes address, wherein the Actinomycetes address includes a polynucleotide probe having the sequence of SEQ ID NO:10. Yet another highly preferred device includes a pan-fungal address, a pan-bacterial address, a Gram$^{(+)}$ address and an Actinomycetes address, wherein the pan-bacterial address includes a polynucleotide probe having a sequence selected from the group consisting of SEQ ID NO:1 and SEQ ID NO:58, wherein the pan-fungal address includes a polynucleotide probe having the sequence of SEQ ID NO:4, wherein the Gram$^{(+)}$ address includes a polynucleotide probe having the sequence of SEQ ID NO:7, and wherein the Actinomycetes address includes a polynucleotide probe having the sequence of SEQ ID NO:10. Still yet another highly preferred embodiment of the invented device has each of the probes labeled with an acridinium ester.

Another aspect of the invention relates to a method of analyzing a biological sample suspected of containing microorganisms. The method begins with a step for obtaining the biological sample. Thereafter there is a step for culturing the biological sample for a period of time sufficient to increase in number any microorganisms contained in the sample. Next, there is a step for releasing polynucleotides from any microorganisms in the cultured biological sample, and then hybridizing the released polynucleotides with a probe matrix. According to some embodiments of the invented method the released polynucleotides have not been amplified in an in vitro polynucleotide amplification reaction. Other embodiments provide for the amplification of polynucleotides, for example by in vitro amplification, prior to the hybridizing step. The polynucleotide probe matrix includes a plurality of addresses with each address including at least one probe that hybridizes ribosomal nucleic acids from one or more microbial species under high stringency conditions. The plurality of addresses includes: a higher-order address, an intermediate-order address, and a lower-order address. The lower-order address hybridizes ribosomal nucleic acids from a subset of organisms having ribosomal nucleic acids that hybridize at the intermediate-order address. The intermediate-order address hybridizes ribosomal nucleic acids from a subset of organisms having ribosomal nucleic acids that hybridize at the higher-order address. Additional steps in the invented method involve detecting positive and negative hybridization results for each of said plurality of addresses to establish a hybridization profile; and then comparing the hybridization profile with a look-up table that correlates the identities of microorganisms with hybridization results at each of the addresses. This procedure provides information about the identity of microorganisms contained in the biological sample. In a preferred embodiment, the salt concentration in the hybridization reaction can be in the range of from 0.6-0.9 M when the hybridization temperature is in the range of from 55-65° C. Regardless of the choice of high stringency conditions that are selected, the higher-order address in the hybridizing step may be a pan-bacterial address that specifically hybridizes ribosomal nucleic acids from a plurality of species of Gram$^{(+)}$ bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*, and the plurality of addresses in the hybridizing step may include a pan-fungal address that specifically hybridizes ribosomal nucleic acids from a plurality of fungal species. When this is the case, and in a preferred embodiment, the intermediate-order address in the hybridizing step can be Gram$^{(+)}$ address that specifically hybridizes ribosomal nucleic acids from a plurality of species of Gram$^{(+)}$ bacteria, and the lower-order address in the hybridizing step can be an Actinomycetes address that specifically hybridizes ribosomal nucleic acids of a plurality of bacteria belonging to the High (G+C) subset of Gram$^{(+)}$ bacteria. Optionally, the biological sample in the obtaining step can be a sample of blood drawn from an individual being tested for a medical condition selected from the group consisting of bacteremia, septicemia and fungemia, and the culturing step may include a step for inoculating a blood bottle with an aliquot of the sample of blood and thereafter incubating the inoculated blood bottle. In a highly preferred embodiment, the detecting step involves detecting by luminometry.

Still another aspect of the invention relates to a method of analyzing a sample containing ribosomal nucleic acids. This method begins with a step for hybridizing the sample with a probe matrix under high stringency conditions to result in a hybridized sample. The probe matrix has a plurality of addresses, including a higher-order address, an intermediate-order address, and a lower-order address. The lower-order address hybridizes ribosomal nucleic acids from a subset of organisms having ribosomal nucleic acids that hybridize at the intermediate-order address. The intermediate-order address hybridizes ribosomal nucleic acids from a subset of organisms having ribosomal nucleic acids that hybridize at the higher-order address. Another step in the invented method involves analyzing the hybridized sample to identify a first collection of addresses having at least one probe complementary to ribosomal nucleic acids present in the sample and to identify a second collection of addresses not having at least one probe complementary to ribosomal nucleic acids present in said sample. Thereafter there is a step for determining from the first and second collections of addresses identified in the analyzing step which of a collection of microorganisms possess ribosomal nucleic acids having a corresponding profile of ribosomal nucleic acid sequences, thereby determining the microbial origin of the RNA containing sample. In a preferred embodiment the higher-order address in the hybridizing step is a pan-bacterial address that specifically hybridizes ribosomal nucleic acids from a plurality of species of Gram$^{(+)}$ bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*, and the plurality of addresses in the hybridizing step further includes a pan-fungal address that specifically hybridizes ribosomal nucleic acids from a plurality of fungal species. When this is the case the intermediate-order address in the hybridizing step can be a Gram$^{(+)}$ address that specifically hybridizes ribosomal nucleic acids from a plurality of species of Gram$^{(+)}$ bacteria, and the lower-order address in the hybridizing step can be an Actinomycetes address that specifically hybridizes ribosomal nucleic acids of a plurality of bacteria belonging to the High (G+C) subset of Gram$^{(+)}$ bacteria. The analyzing step in the invented method may involve analyzing by luminometry. Optionally the hybridizing step is conducted between 55° C. and 65° C.

Still yet another aspect of the invention relates to a device that is used for analyzing results from a probe matrix hybridization procedure. This analytical device includes a memory device having stored therein a look-up table. This look-up table correlates the identities of a plurality of microorganisms with positive and negative hybridization results at a plurality of addresses in a probe matrix. The plurality of addresses includes at least a higher-order address, an intermediate-order address, and a lower-order address. The lower-order address hybridizes ribosomal nucleic acids from a subset of organisms having ribosomal nucleic acids that hybridize at the intermediate-order address. The intermediate-order address hybridizes ribosomal nucleic acids from a subset of organisms having ribosomal nucleic acids that hybridize at the higher-order address. The device also includes a processor linked to the memory device, where the processor is configured to execute a comparison between results inputted into the processor and the look-up table. These results will indicate positive and negative hybridization at the plurality of addresses in the probe matrix for polynucleotides released from the microorganism. The device further includes a user interface linked to the processor for initiating the comparison and an output device linked to the processor for displaying the results of said comparison. In a preferred embodiment the memory device includes magnetic storage media. In a different preferred embodiment the user interface includes a keyboard for inputting into the processor the positive and negative hybridization results. In yet another preferred embodiment the analytical device further includes a probe hybridization detector linked to the processor through an interface for inputting into the processor said positive and negative hybridization results. When this is the case, the detector can include a luminometer. In a highly preferred embodiment the output device is a visual display monitor or a printer.

Still yet another aspect of the invention relates to a method of determining whether a sample of bacteria includes a Staphylococcal species other than *Staphylococcus aureus*. This method begins with a step for releasing polynucleotides from the sample of bacteria to result in a collection of released polynucleotides. Subsequently there is a step for hybridizing the collection of released polynucleotides with a first probe having specificity for ribosomal nucleic acids of bacteria in the genus *Staphylococcus* and with a second probe having specificity for ribosomal nucleic acids of *Staphylococcus aureus*. Thereafter there is a step for detecting any of the first probe or the second probe that hybridized the collection of released polynucleotides. Finally, there is a step for determining that the sample of bacteria contains a Staphylococcal species other than *Staphylococcus aureus* if the first probe hybridized and the second probe did not hybridize.

DETAILED DESCRIPTION OF THE INVENTION

Figure 1:
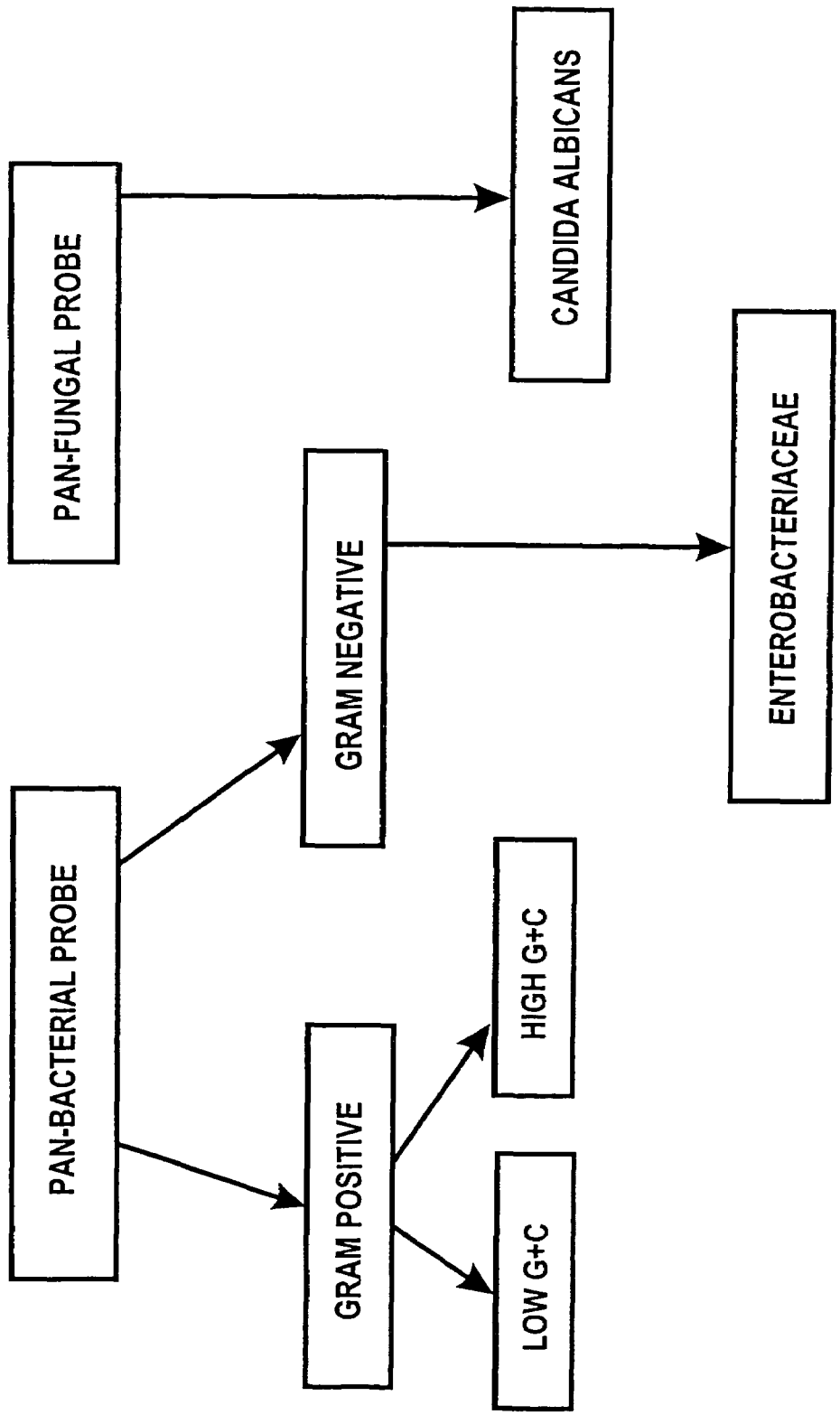
FIG. 1 is a schematic diagram showing a phylogenetic hierarchy. The Enterobacteriaceae are shown as being a subset of the Gram$^{(-)}$ bacteria while the class of Gram$^{(+)}$ bacteria is divided into the Low (G+C) and High (G+C) subsets. A pan-fungal probe identifies organisms that are shown as being unrelated to the organisms identified by a pan-bacterial probe. Arrows indicate phylogenetic relationships.

The present invention relates to polynucleotide-based methods, compositions and devices that can be used to identify microorganisms in a biological sample. The approach detailed herein relies on the use of a "matrix" of polynucleotide hybridization probes. In a preferred embodiment of the invention these hybridization probes are specific for the ribosomal nucleic acids (rRNA and rDNA) of various species or taxonomically related groups of organisms. Using this approach, it is possible to determine the species of an organism from a collection of data that otherwise would produce an ambiguous identification if the hybridization results were considered in isolation from each other. Indeed, even species and strain-level identifications can be made when results from a probe matrix hybridization procedure are analyzed as elements among a set of interrelated results. The below-described method is particularly suited for use in connection with automated microbe identification systems.

Introduction and Background

Herein there is described a matrix-based microbe identification method that employs combinations of polynucleotide probes that hybridize the ribosomal nucleic acids from microorganisms. Probes in the matrix distinguish between organisms that differ from each other by known phylogenetic relationships. For example, probes can be selected to classify organisms as a bacteria or fungi based on the presence or absence of rRNA sequences that distinguish these two types of microorganism. In another example, a probe matrix can employ one or more probes to identify Gram-positive (Gram$^{(+)}$) bacteria in order to distinguish this class from the phylogenetically distinct Gram-negative (Gram$^{(-)}$) bacteria.

Another aspect of the matrix-based method of microbe identification relates to the use of combinations of ribosomal nucleic acid-specific probes in a single hybridization reaction. As described more fully below, even combinations of probes that yield ambiguous results can provide species-level identification when hybridization results from these probe combinations are interpreted in light of other results from the same matrix. For example, a single address in a probe matrix may give a positive hybridization signal when an organism is one of a number of different species. More specifically, a positive hybridization signal at an address in a matrix could indicate that a bacterial isolate is either *S. aureus* or *E. coli*, without indicating which of these possibilities is correct. However, when taken in the context of the additional finding that rRNA from the subject organism hybridized to a probe specific for Enteric bacteria it becomes clear that the organism must be *E. coli* because only *E. coli*, and not *S. aureus*, is classified as an Enteric bacterium. It is to be understood that "Enteric" bacteria are members of the family Enterobacteriaceae. In this way information from matrix-based polynucleotide hybridization procedures can be interpreted unambiguously even down to the level of a species identification.

Even negative results in a probe matrix hybridization procedure can be meaningful when taken in the context of other results from the matrix. For example, if it is determined from a two-locus matrix that a sample contains polynucleotides that give a positive hybridization signal at a first address that identifies pan-bacterial organisms, and give negative results at a second address that identifies both pan-fungal organisms as well as a particular species of bacterium, then the combination of results would indicate that the polynucleotides must have been derived from a bacterial species that is different from the bacterial species that could have produced a positive hybridization signal at the second address in the matrix. This simple example illustrates how the multiplexing aspect of the probe matrix can provide clinically relevant information from a very limited number of loci in a hybridization procedure.

Definitions

As used herein, the following terms have the following meanings unless explicitly stated otherwise.

"Ribosomal nucleic acids" are rRNA and the rDNA that encodes the rRNA.

A "locus" is a place in which something is situated. A locus can be a single well for containing soluble polynucleotides in a multi-well plate; a single spot of immobilized polynucleotides on a piece of nitrocellulose membrane or a dipstick; or a single spot of immobilized polynucleotides on a "DNA chip." Probe molecules disposed at one locus in a testing device do not mingle with probe molecules disposed at another locus in the device.

An "address" refers to one or more polynucleotide probes at a single locus in a testing device, whereby a hybridization result at the address provides discrete information about the presence or absence of complementary polynucleotide sequences among a collection of polynucleotides undergoing testing. For example, an address may provide information about the presence of rRNA that is of bacterial origin. Such information could be derived from a single probe or a cocktail of probes disposed at a single locus on a testing device. An address also may provide information about the presence of rRNA from one or more species of microorganism, such as any of *E. coli, S. aureus, C. albicans, P. aeruginosa* and *S. pneumoniae*. For convenience, an address that detects nucleic acids of a particular organism or type of organism is referred to by the name or type of that organism. Thus, a positive hybridization signal at a "pan-bacterial address" would indicate the presence of ribosomal nucleic acids that are of bacterial origin.

A probe "matrix" is a collection of addresses useful for identifying an unknown microorganism, or for narrowing the range of possible identities of an unknown organism. Probes of the matrix are ordinarily disposed (either by containment of soluble probes or by physical immobilization) at a plurality of physical loci in a testing device, where each locus specifically hybridizes nucleic acids from one or a plurality of microorganism species. At least one locus of the matrix has disposed thereon a lower-order probe that hybridizes nucleic acids from a sub-grouping of microorganisms having nucleic acids that are hybridized by a higher-order probe disposed at a different locus in the matrix. Examples of probes that are considered "higher-order probes" relative to a species-specific probe (as an exemplary phylogenetic classification) include probes having specificity for a taxonomic genus, a taxonomic family or a taxonomic order.

The terms "lower-order address" and "higher-order address" are functionally defined relative to each other. A lower-order address detects ribosomal nucleic acids from a subset of organisms having ribosomal nucleic acids that are detected at a higher-order address. For example, an address that detects a single species of bacteria would be considered a "lower-order address" with respect to another address that detected pan-bacterial organisms.

An "intermediate-order address" is functionally defined as an address that detects ribosomal nucleic acids from a subset of organisms having ribosomal nucleic acids that are detectable at a corresponding higher-order address. The intermediate-order address detects ribosomal nucleic acids from a greater number or range of organisms than the subset of organisms that are detectable at a corresponding lower-order address. For example, with respect to two addresses that independently detect pan-bacterial organisms and the bacterial species *E. Coli*, an address for detecting bacteria in the family Enterobacteriaceae would be an intermediate-order address. This is because the Enterobacteriaceae address detects ribosomal nucleic acids from a subset of the organisms having ribosomal nucleic acids that can be detected at the pan-bacterial address, and because the range of bacterial organisms detected at the Enterobacteriaceae address embraces *E. coli* in addition to other bacterial species.

A "probe" is a single-stranded polynucleotide that combines with a complementary single-stranded target polynucleotide to form a double-stranded hybrid. A probe may be an oligonucleotide or a nucleotide polymer, and may contain a detectable moiety which can be attached to the end(s) of the probe or can be internal to the sequence of the probe. The nucleotides which combine with the target polynucleotide need not be strictly contiguous as may be the case with a detectable moiety internal to the sequence of the probe.

A "detectable moiety" is a molecule attached to, or synthesized as part of, a polynucleotide probe. This molecule should be uniquely detectable and will allow the probe to be detected as a result. These detectable moieties are often radioisotopes, chemiluminescent molecules, enzymes, haptens, redox-active electron transfer moieties such as transition metal complexes, metal labels such as silver or gold particles, or even unique oligonucleotide sequences.

A "hybrid" is the complex formed between two single-stranded polynucleotide sequences by Watson-Crick base pairings or non-canonical base pairings between the complementary bases.

"Hybridization" is the process by which two complementary strands of polynucleotide combine to form a double-stranded structure ("hybrid").

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

"Mismatch" refers to any pairing, in a hybrid, of two nucleotides which do not form canonical Watson-Crick hydrogen bonds. In addition, for purposes of the following discussions, a mismatch can include an insertion or deletion in one strand of the hybrid which results in an unpaired nucleotide(s).

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two polynucleotide strands forming a hybrid. Stringency conditions are chosen to maximize the difference in stability between the hybrid formed with the target and the non-target polynucleotide.

The term "probe specificity" refers to a characteristic of a probe which describes its ability to distinguish between target and non-target sequences. Probe specificity is dependent on sequence and assay conditions and may be absolute (i.e., the probe can distinguish between target organisms and any non-target organisms), or it may be functional (i.e., the probe can distinguish between the target organism and any other organism normally present in a particular sample). Many probe sequences can be used for either broad or narrow specificity determinations depending on the conditions of use.

"Polynucleotide" means either RNA or DNA, along with any synthetic nucleotide analogs or other molecules that may be present in the sequence and that do not prevent hybridization of the polynucleotide with a second molecule having a complementary sequence. The term includes polymers containing analogs of naturally occurring nucleotides and particularly includes analogs having a methoxy group at the 2' position of the ribose (OMe). As used herein, methoxy polynucleotides or oligonucleotides containing "T" residues have a methoxy group at the 2' position of the ribose moiety, and a uracil at the base position of the nucleotide. When particularly specified as "OMeT" it is meant that the base position of the nucleotide is occupied by a thymine residue.

An "oligonucleotide" is a polynucleotide molecule having a length of from 10 to 100 nucleotides, or more preferably 10 to 50 nucleotides. Ordinarily, oligonucleotides will be synthesized by organic chemical methods and will be single-stranded unless specified otherwise. Oligonucleotides can be labeled with a detectable label.

A "helper oligonucleotide" is an oligonucleotide that binds a region of a target polynucleotide other than the region that is bound by an assay probe. These oligonucleotides impose new secondary and tertiary structures on the targeted region of the single-stranded polynucleotide so that the rate of binding of the assay probe is accelerated. Although helper oligonucleotides are not labeled with a detectable label, they facilitate binding of labeled probes and so indirectly enhance hybridization signals.

A "microorganism" or "microbe" is a bacterium, a fungus or a protozoan.

A "pan-bacterial organism" is a microorganism that is classified as a bacterium rather than any other cell type. All *Eubacteria*, but not necessarily *Archaebacteria*, will be classified as pan-bacterial organisms. Yeast or other fungi or eukaryotic organisms are not classified as pan-bacterial organisms.

A "pan-fungal organism" is a microorganism that is classified as a fungus rather than any other cell type. All yeast necessarily will be classified as pan-fungal organisms. Of course, *eubacteria* and *archaebacteria*, which are members of a different taxonomic superkingdom, cannot be classified as pan-fungal organisms.

A "biological sample" refers to a sample of material that is to be tested for the presence of microorganisms. The biological sample can be obtained from an organism, such as a human patient, a laboratory mammal such as a mouse, rat, pig, monkey or other member of the primate family, by drawing a blood sample, sputum sample, spinal fluid sample or a urine sample. Ordinarily, the biological sample will contain hybridizable polynucleotides. These polynucleotides may have been released from organisms that comprise the biological sample, or alternatively can be released from the organisms in the sample using techniques such as sonic disruption or enzymatic or chemical lysis of cells to release polynucleotides so that they are available for hybridization with a polynucleotide probe.

A "confirming result" is a result obtained at one address of a probe matrix that provides information necessary to interpret a different result obtained at a different address in the same probe matrix. For example, if a first result indicates that an organism is either a Gram$^{(+)}$ bacterium or a fungus, then a result indicating that the organism also contained rRNA that hybridizes at a pan-bacterial address would be a confirming result indicating that the organism was a Gram$^{(+)}$ bacterium.

A "look-up table" is a collection of data representing possible combinations of positive and negative hybridization results at each address in a probe matrix hybridization procedure, together with an associated interpretation of each data entry in the collection. A look-up table can be stored on computer-readable media.

Utility of the Matrix-Based Method of Microbe Detection and Identification

The matrix-based method of identifying microorganisms is broadly useful for clinical laboratory testing, food testing and environmental testing. The invention can be used to identify organisms that have been cultured, but growth of the organism on specialized media is not required for determining the identity of the organism. The system is particularly useful for the rapid clinical diagnosis of microbial infections, including infections of the oral cavity, blood stream (septicemia and fungemia), genitals and perigenital tissue, urinary tract, gastrointestinal tract, traumatic and surgical wounds, cardiac tissue (infective endocarditis), ocular, auditory apparatus, and cerebral spinal fluid. The system is also useful for monitoring the presence of potentially harmful microbes in immunocompromised individuals, such as individuals infected with HIV or those treated with immunosuppressant drugs employed in bone marrow transplantation, even if the individual displays no symptoms of infection. Similarly, the invented methods are useful for detecting infection in the context of veterinary diagnoses of domesticated animals (e.g., bovine mastitis).

The present invention can be used for detecting the presence of one or more types of microbes in environmental samples. For example, the invention can be used for monitoring the efficacy of municipal water treatment or the level of contaminants in recreational water sources. Testing of environmental samples according to the methods described herein allows the detection of undesirable microbes in aqueous or non-aqueous systems. Microbes of particular interest in this aspect of the invention cause corrosion, biomass accumulation, or are involved in breakdown processes of pipelines, storage tanks or processing facilities. Testing of environmental water samples for microbes which positively or negatively impact manufacturing processes, such as the production of paper, textiles, and electronic components can also be performed using the methods described herein. The invention also can be used for detecting microbes in food or agricultural samples. Organisms of particular interest in connection with this aspect of the invention may be used for preventing disease, or as indicators of environmental contamination. In addition to monitoring samples for harmful microbes (i.e., contaminants), the present invention can also be used for detecting, identifying and quantifying beneficial microbes, such as those that occur in naturally fermented foods and beverages.

Additionally, the methods detailed below can be used for discovering new antimicrobial therapeutics. More particularly, the matrix-based methods of microbe identification can be used for rapidly monitoring whether candidate antimicrobial agents prevent or inhibit microbial growth in vitro or in vivo. Still further, the invented method can be used for monitoring the susceptibility of an organism to an antibiotic, either in a mixed culture or as a purified isolate.

Minimal Probe Matrices

According to the method disclosed herein, a biological sample containing polynucleotides is hybridized to a collection of polynucleotide probes, each of these probes having binding specificity for a ribosomal nucleic acid of at least one microbe. The collection of probes is organized into a series of "addresses" that provide information about the presence or absence of one or more polynucleotide sequences in a sample containing nucleic acids. Significantly, in vitro amplification of ribosomal nucleic acid sequences is not required for success of the method disclosed herein. Indeed, while in vitro amplification of rRNA or rDNA sequences optionally can be performed prior to the hybridizing step, it is preferred that polynucleotides released from the biological sample are hybridized to the collection of polynucleotide probes without a prior amplification step. Following the hybridization procedure, each of the addresses is analyzed to assess whether a positive or negative hybridization result was obtained.

A minimal probe matrix includes two loci and has a single probe disposed at a first locus and a plurality of probes disposed at the second locus. An exemplary first address in a probe matrix could be used for detecting rRNA from any bacterial organism. An exemplary second address can be used for detecting the rRNA from any fungal organism as well as Gram$^{(+)}$ bacteria. This could be accomplished by depositing in the first well of a 96-well microtiter plate a polynucleotide probe that hybridizes a rRNA segment that is conserved among all species of bacteria. A second well would contain the combination of a probe that hybridizes a rRNA segment that is conserved among all species of fungi, and a probe that hybridizes the rRNA of Gram$^{(+)}$ but not Gram$^{(-)}$ bacteria. This two-locus matrix, when hybridized with polynucleotides isolated from a single, well isolated colony of organisms would provide answers to three questions. More particularly, the exemplary two-locus matrix would be able to indicate whether the organism was bacterial in origin; whether a bacterial organism was a Gram$^{(+)}$ or Gram$^{(-)}$ bacterium; and whether the organism was a fungus (which is mutually exclusive of a bacterial identification for a unimicrobial system).

The fact that these three questions can be answered unambiguously by analyzing the results obtained from only two loci illustrates how a matrix approach can be used to maximize the value of output data from a very simple testing device. Since each of the two loci will produce one of two results, that is either a positive or a negative result, the number of possible outcomes will be the number of possible results at each locus (2) raised to the power of the number of loci in the matrix (2). Thus, for a two-locus matrix there will be $2^2$ or 4 possible outcomes. The interpretation of these results can be understood by reference to Table 1 wherein positive hybridization results are indicated by "(+)" and negative hybridization results are indicated by "(−)."

TABLE 1

Interpretation of Results from an Illustrative Two-Locus Matrix

|  | (pan-fungal/Gram$^{(+)}$) (−) | (pan-fungal/Gram$^{(+)}$) (+) |
|---|---|---|
| pan-bacterial (−) | (−/−): absence of bacteria or fungi | (−/+): fungal organism |
| pan-bacterial (+) | (+/−): Gram$^{(-)}$ bacteria | (+/+): Gram$^{(+)}$ bacteria |

The information in Table 1 represents a form of "look-up" table that can be used to decode a profile of hybridization results in order to identify the type of organism that is under study. If a species-specific probe for *E. coli* is substituted for the Gram$^{(+)}$ probe in the above Example, then the modified two-locus matrix would be useful for determining whether an organism is a bacterium or a fungus, and whether any detected bacteria is *E. coli*.

Results from a probe matrix hybridization procedure can be inputted into a computer or data processor ("computer"), either manually using a keyboard or directly through an interface from an automated device such as a plate reader, film scanner or luminometer. The computer can sort the positive and negative hybridization results for a particular organism to establish a profile. This profile can then be compared with a look-up table stored in a memory device linked to the computer to associate the hybridization profile with hybridization results obtained using control organisms in order to determine the identity, or candidate identity in the case of ambiguous results that are characteristic of more than one organism, of the organism that was used to conduct the procedure.

For example, a computer linked to a luminometer through an interface can have stored in a memory device a look-up table for the four possible outcomes shown in Table 1. In response to receiving an input representing the (+/+) hybridization result, an algorithm used by the computer would compare the result with the look-up table and provide an output indicating that the organisms under study were Gram$^{(+)}$ bacteria. Alternative results for the inputs (−/−), (+/−) and (−/+) would respectively prompt outputs indicating the absence of bacterial or fungal hybridizing polynucleotide species, the presence of bacteria other than Gram$^{(+)}$ bacteria, and the presence of a fungal organism. A similar process for decoding more complex matrices having more than two loci can be carried out using the same procedure. It should be apparent that more complex matrices will provide a more complete identification of organisms.

In another illustration of the probe matrix-based method, a third locus for detecting particular microorganism species can be added to the two-locus matrix described above. More particularly, the first locus can provide information about the presence of pan-bacterial rRNA sequences; the second locus can provide information about hybridization of a pan-fungal probe and a probe for Gram$^{(+)}$ bacteria; and a third locus can provide information about the identity of certain species of bacteria and fungi. An illustrative third locus could have species-specific probes for *E. coli, Staphylococcus aureus, Candida albicans, Pseudomonas aeruginosa* and *Streptococcus pneumoniae*. Table 2 presents the expected outcomes for hybridization results using this three-locus matrix. Since each of the three loci provides one of two results, the number of entries in the Table is given by $2^3$ or 8. Again, the results presented in the following Table assume a pure culture of a single type of organism.

TABLE 2

Interpretation of Results from an Illustrative Three-Locus Matrix

| Pan-bacterial/Pan-fungal & Gram$^{(+)}$/Species probes | Interpretation |
|---|---|
| (−/−/−) | No bacteria or fungi detected |
| (+/−/−) | Gram$^{(-)}$ bacteria detected |
| (+/+/−) | Gram$^{(+)}$ bacteria detected; but not *S. aureus* or *S. pneumoniae* |
| (+/+/+) | Gram$^{(+)}$ bacteria detected is either *S. aureus* or *S. pneumoniae* |
| (−/−/+) | Result is not meaningful |
| (−/+/−) | Fungus other than *C. albicans* detected |
| (−/+/+) | *C. albicans* detected |
| (+/−/+) | Bacteria detected as either *E. coli* or *P. aeruginosa* |

The information presented in Table 2 represents a look-up table that can be used to interpret any result obtained with the exemplary three-locus matrix. Again, it should be apparent that the results obtained using a three-locus matrix are sufficient to provide a greater range of identifying information when compared with a matrix that differs by only a single locus. In the above example, the three-locus matrix was sufficient to: (1) classify an organism as being either bacterial or fungal; (2) identify bacteria as either Gram$^{(+)}$ or Gram$^{(-)}$; (3) determine whether or not the species of a fungus is *C. albicans*; (4) indicate whether a Gram$^{(-)}$ bacterium is either *E. coli* or *P. aeruginosa*; (5) indicate whether a Gram$^{(+)}$ bacterium is either *S. aureus* or *S. pneumoniae*, (6) indicate whether a bacteria culture that is not Gram$^{(+)}$ is either *E. coli* or *P. aeruginosa*.

Significantly, the results presented in Table 2 show that it is acceptable to have entries in the look-up table that are ambiguous because these results can still be meaningful in the diagnosis of infection. For example, the "(+/+/−)" result in the Table indicated that the organism was a Gram$^{(+)}$ bacteria other than *S. aureus* or *S. pneumoniae*. Thus, it is allowable to use an ambiguous identification scheme to exclude certain organisms from a diagnosis. Similarly, it is allowable to identify an organism as being one of a number of different species of organism and still achieve a clinically meaningful result that can be used to determine an appropriate antibiotic therapy. This is illustrated by the "(+/−/+)" result in Table 2, which indicated that a bacterial organism was one of two candidates.

Additionally, the results in Table 2 show that it is acceptable to have entries in the look-up table that are not meaningful. In this instance, the result "(−/−/+)" was not meaningful because it would not be possible to achieve a positive hybridization result at the third locus without also having a positive hybridization result at at least one of the first two loci. Thus, it is allowable to have possible probe matrix hybridization results that are not meaningful. However, we note that an *Archaebacteria* probe that does not cross-react with the rRNA of *Eubacteria* could be disposed among the collection of species-specific probes in the third address and would give meaning to the "(−/−/+)" result.

Clearly, a probe matrix having as few as two addresses can provide useful information about the identity of an organism under investigation. For example, if the first address detects bacterial organisms and the second address detects fungal organisms, then this two-address matrix would be useful for determining whether an organism was bacterial or fungal. Adding a third address to the matrix would provide additional information and would expand the utility of the matrix. An exemplary third address would distinguish the rRNA of Gram$^{(+)}$ and Gram$^{(-)}$ bacteria, for example by detecting the rRNA of Gram$^{(+)}$ bacteria. Thus, a result with a three-address matrix that indicated positive hybridization results for a pan-bacterial probe and a Gram$^{(+)}$ probe, but negative results with a pan-fungal hybridization probe would indicate the presence of Gram$^{(+)}$ bacteria and the absence of fungi. Adding a fourth address to the matrix provides even greater functionality. An exemplary fourth address would detect bacteria in the Actinomycetes subset of Gram$^{(+)}$ bacteria. Addition of a fifth address to the matrix could be used to identify organisms that are Enteric bacteria or members of the genus *Enterococcus*. This could be accomplished using a plurality of rRNA-specific probes that give positive hybridization signals when either of these two types of bacteria is present. Notably, in separate preferred embodiments of the invention the probes having specificity for rRNA of *Enterococcus* or Enteric bacteria are disposed at different loci and at a common locus in a testing device. A sixth address could be used to identify bacteria that are in the *Staphylococcus* genus and *Campylobacter* group. Again, in separate preferred embodiments of the invention the probes having specificity for rRNA of the *Staphylococcus* genus and the *Campylobacter* group of bacteria are disposed at different loci and at a common locus in a testing device. A seventh address representing a collection of species-specific probes can provide information adequate to identify particular species with certainty. For example, the seventh address could include species-specific probes for *E. coli, Staphylococcus aureus, Candida albicans, Pseudomonas aeruginosa* and *Streptococcus pneumoniae*. Even though these species represent very different organisms, it will be apparent that any positive hybridization result with a species-specific probe at the seventh address must be interpreted in combination with, or in the context of all other results observed at the other addresses in the matrix. The same is true for negative hybridization results observed at the seventh address. Each of the foregoing exemplary matrices represents a preferred embodiment of the invention. Of course, it is to be understood that probes can have binding specificity for either rRNA or rDNA even though the foregoing exemplary cases have particularly referred to rRNA-specific probes.

Matrix-Based Methods of Identifying an Organism

A key feature of the matrix-based hybridization method concerns the relationship between constituent addresses that comprise the matrix. Preferred probe matrices include a combination of "higher-order" and "lower-order" addresses. A higher-order address is always used for identifying more than one species of organism and will fully embrace organisms that are identified at at least one other address in the same matrix. Thus, an address that identifies the Actinomycetes subset of Gram$^{(+)}$ bacteria would be considered a lower-order address with respect to a different address specific for the broader category of Gram$^{(+)}$ bacteria. The same relationship characterizes addresses useful for identifying Gram$^{(+)}$ bacteria and pan-bacterial organisms. Advantageously, redundancy inherent in the ability of a particular rRNA or rDNA species to hybridize at more than one address in a probe matrix means that both positive and negative hybridization results are informative. Probe matrices that comprise three addresses may include an intermediate-order address in addition to the higher-order and lower-order addresses.

It is preferred that higher-order, intermediate-order and lower-order addresses are related by a hierarchy of molecular taxonomy. Higher-order addresses identify broad categories of microorganism cell types. For example, a higher-order address could be used for identifying pan-bacterial organisms. An intermediate-order address could identify the subset of Gram$^{(+)}$ bacteria. A lower-order address could then identify the Actinomycetes subset of Gram$^{(+)}$ bacteria. Still a lower-order address could identify a particular species that is a member of the Actinomycetes, such as *Streptococcus pneumoniae*.

Results from probe matrix-based hybridization procedures indicate whether or not target nucleic acids positively hybridize at pre-selected addresses. Since the polynucleotide probe(s) representing a particular address allowably may contain mismatches with positively hybridizing target sequences, it is to be understood that a positive hybridization signal does not necessarily indicate that the complementary sequence of the probe is found in the target nucleic acid sequence. This may be the case in instances wherein a single hybridization probe is employed to identify a collection of microorganisms, such as pan-bacterial organisms or a genus of bacteria. However, it also should be understood that in certain cases a positive hybridization result will indicate a precise correspondence between the sequence of a probe and the complementary sequence found in the target polynucleotide. This frequently will be true for cases that involve species-specific probes. In such instances it is desirable to have a probe that particularly hybridizes only a single type of target nucleic acid.

The results from probe matrix hybridization procedures are most informative when interpreted in the context of other results from the same procedure. A positive hybridization result at a higher-order address indicates that a test organism is a member of the group of organisms identified at that address. For example, a positive hybridization result at an address that identifies pan-bacterial organisms indicates the test organism is bacterial, but provides no additional information regarding the identity of the organism. A positive hybridization result at an intermediate-order address indicates the test organism is a member of the subset of organisms identified at the higher-order address that also are members of the collection of organisms identified at the intermediate-order address. Of course, a positive hybridization result at the higher-order address and a negative hybridization result at the intermediate-order address would mean that the test organism cannot be among the group of organisms identified at the intermediate-order address. For example, positive hybridization results at pan-bacterial and Gram$^{(+)}$ addresses in a probe matrix would indicate that an organism was a member of the Gram$^{(+)}$ subset of bacteria. A negative hybridization result would indicate the organism must be different from an organism that otherwise could have produced a positive hybridization result. Thus, a negative hybridization result at an address for detecting Gram$^{(+)}$ bacteria would indicate that the test organism was not a Gram$^{(+)}$ bacterium. Finally, a positive hybridization result at a lower-order address indicates the test organism is a member of the group of organisms identified by that lower-order address. If the lower-order address corresponds to a particular species, then the positive result identifies the species of the test organism.

Of course, those having an ordinary level of skill in the art will appreciate that the higher-order/intermediate-order/lower-order relationship among addresses in a probe matrix is a relative one. While a Gram$^{(+)}$ address is higher-order with respect to an Actinomycetes address (because the Actinomycetes represent a subset of Gram$^{(+)}$ organisms), a Gram$^{(+)}$ address also can be considered to be lower-order with respect to an address that identifies pan-bacterial organisms (because Gram$^{(+)}$ organisms represent a subset of pan-bacterial organisms). However, in the context of a three-address probe matrix that includes a pan-bacterial address, a Gram$^{(+)}$ address and an Actinomycetes address, the Gram$^{(+)}$ address would be considered to be an intermediate-order address because of its relationship to the other addresses in the matrix.

The aggregated collection of positive and negative results from a probe matrix hybridization procedure can be interpreted to provide information about the identity of an organism that is present in the biological sample. Significantly, negative results are highly informative in the context of the probe matrix. In many instances it will be possible to determine the species-level identity of an organism. However, it is not always necessary to achieve a species-level identification in order to obtain useful information. Merely determining the broad taxonomic features of an organism, or even excluding one or more species from a collection of candidate organisms can be highly informative in a clinical setting.

Indeed, it may be highly informative to determine whether an organism responsible for infection is a bacterium or a fungus. This basic information would be useful for determining whether an anti-bacterial agent or an anti-fungal agent should be used for treating an infection. Alternatively, it may be useful to establish whether a bacterial infection is caused by a Gram$^{(+)}$ or a Gram$^{(-)}$ organism because infections caused by these two types of bacteria commonly are treated with different antibiotic regimens and have different clinical prognoses. Another advantage of the matrix-based approach for identifying microbes relates to the rapidity with which results are obtained.

In clinical laboratory practice it is often necessary to obtain a biological sample from a patient having an infection for which the causative organism must be identified. The biological sample may be in the form of a swab or a sample of body fluid. For example, the sample may be a sputum sample if the patient is afflicted with a respiratory infection or a blood sample if bacteremia or septicemia is suspected. The biological sample may then be cultured for a period of time so that the number of organisms is increased as a result of growth of the organism. Metabolic or biochemical testing then can be undertaken to gain further information about the cultured organism.

The matrix-based approach for identifying microbes differs from conventional approaches in several respects. Rather than being conducted as a series of independent tests, the matrix hybridization is carried out simultaneously and preferrably on the same platform so that it is unnecessary to obtain a result from a first test before selecting and initiating a second test. As indicated above, negative results in the matrix are meaningful because they are interpreted against a background of positive hybridization results.

Significantly, the probe matrix approach described herein can resolve the identity of an organism from a collection of data that otherwise would yield only an ambiguous identification. In some instances an address in a probe matrix may indicate whether a biological sample contains rRNA that hybridizes one of several different polynucleotide probes. For example, a single address in a probe matrix may contain species-specific probes for *E. coli, S. aureus, C. albicans, P. aeruginosa* and *S. pneumoniae*. A positive hybridization signal at this address would ambiguously indicate the presence of one or more of these five species of microorganism. However, when confirming results from other addresses in the matrix are considered, the origin of the hybridizing rRNA can be clarified. For example, when taken in view of a positive hybridization result at an address corresponding to a pan-bacterial probe and a negative hybridization result at an address representing a pan-fungal probe, it would be clear that the organism could not be the yeast *C. albicans* because the pan-fungal probe gave a negative hybridization signal. When taken further in view of a positive hybridization signal at an address for Gram$^{(+)}$ bacteria, it becomes clear that the microorganism cannot be *E. coli* or *P. aeruginosa* because these organisms are Gram$^{(-)}$ bacteria. Thus, the biological sample undergoing testing must be either *Staphylococcus aureus* or *Streptococcus pneumoniae*. Finally, if these aggregated results are taken still further in view of a positive hybridization signal at an address representing the *Staphylococcus* genus or *Campylobacter* groups of bacteria, it becomes clear that the organism contained in the biological sample must be *S. aureus* because *S. pneumoniae* is neither a Staphylococcal nor a *Campylobacter* organism. In this manner it is possible to arrive at an unambiguous conclusion about the identity of an organism when presented with a collection of otherwise ambiguous results.

Ribosomal Nucleic Acids as Indicators of the Presence of an Organism

It is generally true that the presence of a microorganism in a biological sample will be indicated if the biological sample also contains rRNA or rDNA that is characteristic of the microorganism. Thus, the presence of a particular rRNA in a biological sample is diagnostic of the presence of a microorganism that produces that rRNA. If a hybridization reaction gives a positive result with a probe specific for Gram$^{(+)}$ bacteria, that result would indicate the presence of one or more species of Gram$^{(+)}$ bacteria in the biological sample. In contrast, a negative result would indicate the absence of Gram$^{(+)}$ bacteria. Of course, a series of positive and negative control hybridizations can be carried out in parallel to ensure validity of the testing results.

Molecular Phylogenetic Relationships for Detecting and Identifying Microorganisms Matrix-based methods of identifying a microorganism preferably employ polynucleotide probes corresponding to addresses that distinguish the ribosomal nucleic acids of organisms according to known molecular phylogenetic relationships. Probes useful for making these distinctions are referred to herein as "taxonomic differentiators." It is an object of the invention to employ an optimal set of polynucleotide probes for discriminating between the molecular phylogenetic divergence points that distinguish ribosomal nucleic acids from different species and groups of microorganisms.

When a probe matrix is constructed using addresses that are related by a hierarchy of molecular taxonomy, it becomes possible to classify in clinically relevant detail the characteristics of microorganisms based on only a minimal number of hybridization probes. Again, this feature of the invention is possible because both positive and negative hybridization results are meaningful in the context of a probe matrix hybridization procedure.

The phrase "hierarchy of molecular taxonomy" is used herein to refer to relationships between organisms at the kingdom, phylum, class, order, family, genus, sub-genus, species and strain-levels that can be detected by virtue of related nucleic acid sequences. For example, a particular bacterial species may have a ribosomal nucleic acid sequence that includes a unique domain (that would be diagnostic of the species) and a shared domain that is common to a genus of bacteria. This hierarchical relationship among addresses contributes to the broad utility of the probe matrix-based method of identifying microorganisms.

Preferred probe matrices have at least one higher-order address and at least one lower-order address. Other preferred probe matrices further include at least one intermediate-order address. Still other preferred probe matrices further include both at least one intermediate-order address, and at least one address specific for an organism that belongs to a taxonomic superkingdom that is different from the superkingdom that embraces organisms identifiable at the higher-order address. For example, if the higher-order address in a particular probe matrix identifies pan-bacterial organisms (which are members of the superkingdom *Procaryotae*), then an example of an address specific for an organism in a different taxonomic superkingdom would be an address for organisms from the superkingdom *Eukaryotae* (which includes Kingdom *Fungi*, Kingdom *Protoctista*, Kingdom *Animalia*, and Kingdom *Plantae*). When higher-order, intermediate-order and lower-order addresses in a probe matrix identify bacterial organisms, a fourth address in certain preferred matrices identifies fungal organisms.

Numerous three-address probe matrices can be made and used according to the procedures described herein. Table 3 provides functional descriptions of some addresses that can be used in different three-address probe matrices.

TABLE 3

Functional Descriptions of Illustrative Three-Address Matrices

| Higher-Order Address | Intermediate-Order Address | Lower-Order Address |
|---|---|---|
| Identifies a collection of organisms | Identifies a subset of organisms that can be identified at the higher-order address | Identifies a subset of organisms that can be identified at the intermediate-order address |
| family | genus | sub-genus |
| genus | sub-genus | species |
| pan-bacterial | bacterial family | bacterial species |

Table 3 illustrates functional relationships between higher-order, intermediate-order and lower-order addresses in a collection of three-address matrices. Generally, the lower-order address identifies a subset of organisms that can be identified at the intermediate-order address, and the intermediate-order address identifies a subset of organisms that can be identified at the higher-order address in the probe matrix. This relationship would characterize a probe matrix having addresses for: (1) pan-bacterial organisms, (2) organisms falling within the genus *Staphylococcus*, and (3) the species *S. aureus*. In another example, the higher-order address can identify organisms belonging to a taxonomic family, the intermediate-order address can identify organisms belonging to a taxonomic genus, and the lower-order address can identify organisms belonging to a sub-genus. The same pattern of relationships holds for addresses that identify organisms belonging to a genus, a sub-genus, and a particular bacterial species. Of course, the higher-order address can identify organisms from a particular Kingdom, such as Kingdom *Procaryotae* which embraces all bacteria. Indeed, probe matrices that include a pan-bacterial address are highly preferred in the present invention.

Illustrative Taxonomic Differentiators

Organisms giving positive hybridization results at a pan-bacterial address include all bacteria hybridizing at a Gram$^{(+)}$ address, an Actinomycetes address, an address that detects bacteria in the family Enterobacteriaceae, an address that detects bacteria in the genus *Staphylococcus*, an address that detects *Campylobacter* species, or bacterial species addresses in the matrix. The pan-bacterial address will not hybridize nucleic acids of fungal organisms.

Organisms producing positive hybridization results at a pan-fungal address include *Candida albicans* and other fungal species, but not bacterial organisms.

The distinction between Gram$^{(+)}$ and Gram$^{(-)}$ bacteria can be made in either of two ways. First, a positive hybridization signal at an address specific for Gram$^{(+)}$ bacteria can indicate that an organism is a Gram$^{(+)}$ bacterium and not a Gram$^{(+)}$ bacterium. Second, a positive hybridization signal at an address specific for Gram$^{(-)}$ bacteria can indicate that an organism is a Gram$^{(-)}$ bacterium and not a Gram$^{(+)}$ bacterium. As illustrated in the working Examples herein, an address specific for Gram$^{(+)}$ bacteria was conveniently used to make this distinction. Organisms giving positive hybridization results at the Gram$^{(+)}$ address include the Actinomycetes, bacteria classified among the genus *Staphylococcus*, bacteria among the genus *Enterococcus*, but not bacteria in the family Enterobacteriaceae.

The Actinomycetes, or the "High (G+C)" subset of Gram$^{(+)}$ bacteria, are a distinct evolutionary lineage within the eubacteria. The Actinomycetes exhibit highly unusual phenotypic features as a reflection of a characteristically high mutation rate. Many members of this group of bacteria produce antibiotics and are commonly found in soil. Actinomycetes bacteria are responsible for a variety of significant animal diseases including tuberculosis, leprosy, diphtheria and periodontal diseases. The genera *Corynebacterium* and *Mycobacterium* are examples of Actinomycetes that are important human pathogens. Immunodeficient individuals are particularly susceptible to infection by the *Mycobacteria avium*, *Mycobacteria intracellulare*, and *Mycobacteria scrofulaceum*, all of which are individual species among the Actinomycetes. The Actinomycetes include: *Corynebacterium aquaticum*, *Corynebacterium jeikieum*, *Corynebacterium xerosis*, *Micrococcus luteus*, *Propionibacterium acnes*, *Mycobacterium chelonae*, *Mycobacterium terrae*, *Mycobacterium intracellulare*, *Mycobacterium simiae*, *Mycobacterium avium*, *Mycobacterium scrofulaceum*, *Mycobacterium gordonae*, *Mycobacterium kansasii*, *Mycobacterium smegatis*, *Mycobacterium fortuitum*, *Mycobacterium gastri*, *Mycobacterium xenopi*, *Mycobacterium marinum* and *Mycobacterium phlei*.

Members of genera belonging to the family Enterobacteriaceae are among the most pathogenic and most frequently encountered organisms in clinical microbiology. These large Gram$^{(-)}$ rods cause many types of human infections, including abscesses, pneumonia, meningitis, bacillary dysentery, typhoid, septicemia and food poisoning. Because many different species in this family can cause similar symptoms, biochemical or nucleic acid testing is crucial for the identification, diagnosis, and treatment of infection. The family Enterobacteriaceae includes: *Citrobacter diversus*, *Citrobacter freundii*, *Enterobacter aerogenes*, *Enterobacter agglomerans*, *Enterobacter cloacae*, *Enterobacter fragilis*, *Enterobacter gergoviae*, *Escherichia coli*, *Escherichia fergusonii*, *Escherichia hermanii*, *Hafnia alvei*, *Klebsiella oxytoca*, *Klebsiella ozaenae*, *Klebsiella pneumoniae*, *Klebsiella rhinoscleromatis*, *Proteus mirabilis*, *Proteus penneri*, *Proteus vulgaris*, *Providencia alcalifaciens*, *Providencia rettgeri*, *Providencia stuartii*, *Salmonella enteritidis*, *Salmonella paratyphi*, *Salmonella typhi*, *Salmonella typhimurium*, *Serratia liquefaciens*, *Serratia marcescens*, *Shigella dysenteriae*, *Shigella sonnei*, *Yersinia enterocolitica*, *Yersinia intermedia*, *Yersinia pseudotuberculosis* and *Morganella morganii*.

Bacteria that are members of the genus *Enterococcus* are part of the normal flora of the gastrointestinal tract, but can cause infection of the urinary tract, wounds, peritonitis, septicemia and endocarditis. This genus is subdivided into three groups composed of the following species: Group I, *E. avium, E. pseudoavium, E. malodoratus,* and *E. raffinosus*; Group II, *E. faecalis, E. solitarius, E. gallinarum, E. faecium, E. casseliflavus* and *E. mundtii*; Group III, *E. durans, E. hirae* and *E. faecalis* (asac). To date, there has only been one isolate of *E. solitarius*, the type strain of the species. A recent national study of *enterococci* isolated from human infections indicated that isolates of *E. faecalis* and *E. faecium* comprised 98% of the samples (Fackiam et al., 1985. Chapter 16. *Streptococci* and *aerococci*, p. 154-175. In Lennette et al., (eds.) Manual of Clinical Microbiology, Fourth Edition. American Society for Microbiology, Washington, D.C.). Bacteria falling under the genus *Enterococcus* include: *E. avium, E. pseudoavium, E. malodoratus, E. raffinosus, E. faecalis, E. solitarius, E. gallinarum, E. faecium, E. casseliflavus, E. mundtii, E. durans* and *E. hirae*. The probe used in the procedures described herein specifically detected all species of *Enterococcus* except for *E. solitarius*.

The genus *Staphylococcus* is divided into two major groups: aureus and non-aureus. *S. aureus* is a cause of soft tissue infections, as well as toxic shock syndrome (TSS). This organism can be distinguished from other species of *Staphylococcus* by a positive result in a coagulase test (all other species are negative). The pathogenic effects of *Staphylococcus* are mainly associated with the toxins it produces. The *S. aureus* enterotoxin causes quick onset food poisoning which can lead to cramps and severe vomiting. Infection frequently can be traced to contaminated meats which have not been fully cooked. These microbes also secrete leukocidin, a toxin which destroys white blood cells and leads to the formation of puss and acne. More specifically, *S. aureus* has been found to be the causative agent in such ailments as pneumonia, meningitis, boils, arthritis, and osteomyelitis (chronic bone infection). Bacteria falling under the genus *Staphylococcus* include: *Staphylococcus aureus, Staphylococcus cohnii, Staphylococcus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulans* and *Staphylococcus warneri*.

Organisms classifiable as *Campylobacter* species are $Gram^{(-)}$ bacteria that cause 5-11% of all diarrhea cases in the United States. These organisms achieve cell motility through polar flagella which emanate from the curved rod-shaped cell. The most commonly isolated species of *Campylobacter* is *C. jejuni*, an organism that causes gastrointestinal infection. Humans commonly acquire the organisms by eating undercooked chicken or drinking contaminated milk and water. Infection usually leads to fever, cramps, and bloody diarrhea. This organism also can cause septicemia in humans. Bacteria classifiable as *Campylobacter* species include: *Campylobacter jejuni, Campylobacter coli* and *Campylobacter laridis*.

While criteria such as morphology, color and metabolic requirements can be used to characterize the phylogenetic relationships among organisms, a particularly useful set of relationships that lend themselves to molecular genetic analysis have been identified in the course of developing the invention. These relationships are illustrated in FIGS. 1-3.

As indicated in FIG. 1, polynucleotide probes at "pan-bacterial" and "pan-fungal" addresses are useful for determining whether a biological sample contains ribosomal nucleic acids that are of bacterial or fungal origin. Microorganisms in the bacterial lineage can be subdivided as $Gram^{(+)}$ or $Gram^{(-)}$ at an address corresponding to a polynucleotide probe that specifically hybridizes ribosomal nucleic acids from $Gram^{(+)}$ bacteria, but not the ribosomal nucleic acids from $Gram^{(-)}$ bacteria. Interestingly, it is known that some bacteria within the class of $Gram^{(+)}$ bacteria have lost the trait that confers the ability to stain positively in the Gram-staining procedure. These bacteria would erroneously be classified as $Gram^{(-)}$ by staining, but have retained the molecular phylogenetic characteristics of $Gram^{(+)}$ bacteria at the polynucleotide sequence level. A particularly useful taxonomic differentiator involves the subdivision of $Gram^{(+)}$ bacteria into the "Low (G+C)" and the "High (G+C)" or "Actinomycetes" groups at an address that identifies the Actinomycetes. It is to be understood that this categorization of bacteria refers to the total genomic molar percentage of guanine and cytosine (G+C). FIG. 2 particularly illustrates how several clinically relevant bacteria can be typed down to the genus- and even species-level after having been sub-categorized as members of the High (G+C) or Low (G+C) groups of $Gram^{(+)}$ bacteria. The Figure also shows how *Enterococcus* bacteria can be classified as members of the Low (G+C) group of $Gram^{(+)}$ bacteria. FIG. 3 illustrates a scheme for sub-classifying numerous species of $Gram^{(-)}$ bacteria. The Figure particularly shows how several different bacterial species, including *E. Coli*, share a common molecular phylogenetic relationship as members of the group of Enterobacteriaceae or "Enteric bacteria."

Figure 2:
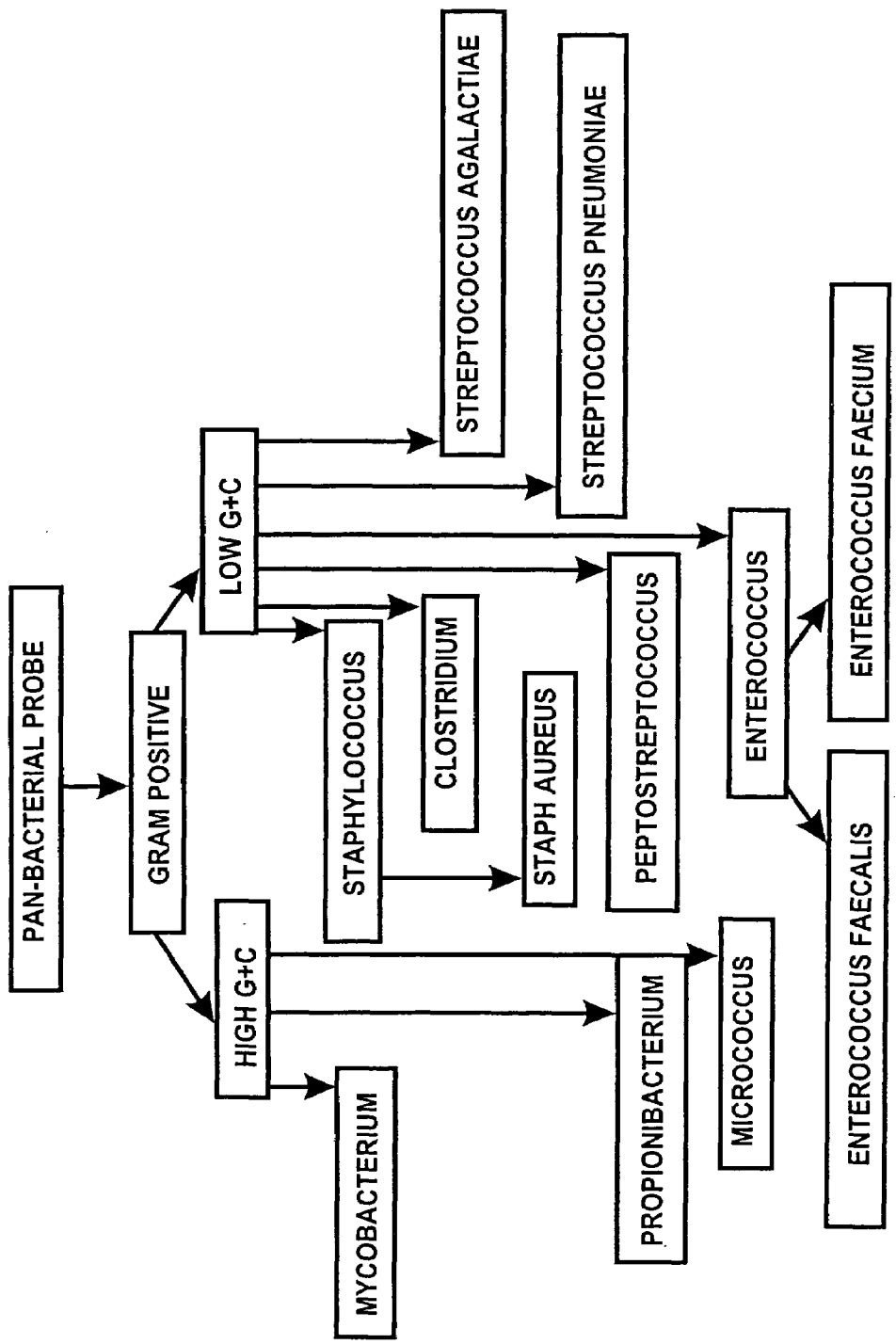
FIG. 2 is a schematic diagram showing the phylogenetic hierarchy among the Gram$^{(+)}$ bacteria. The High (G+C) subset of Gram$^{(+)}$ bacteria is shown as including the Mycobacteria while the Low (G+C) subset of Gram$^{(+)}$ bacteria includes *Staphylococcus, Streptococcus* and *Enterococcus*. Arrows indicate phylogenetic relationships.
Figure 3:
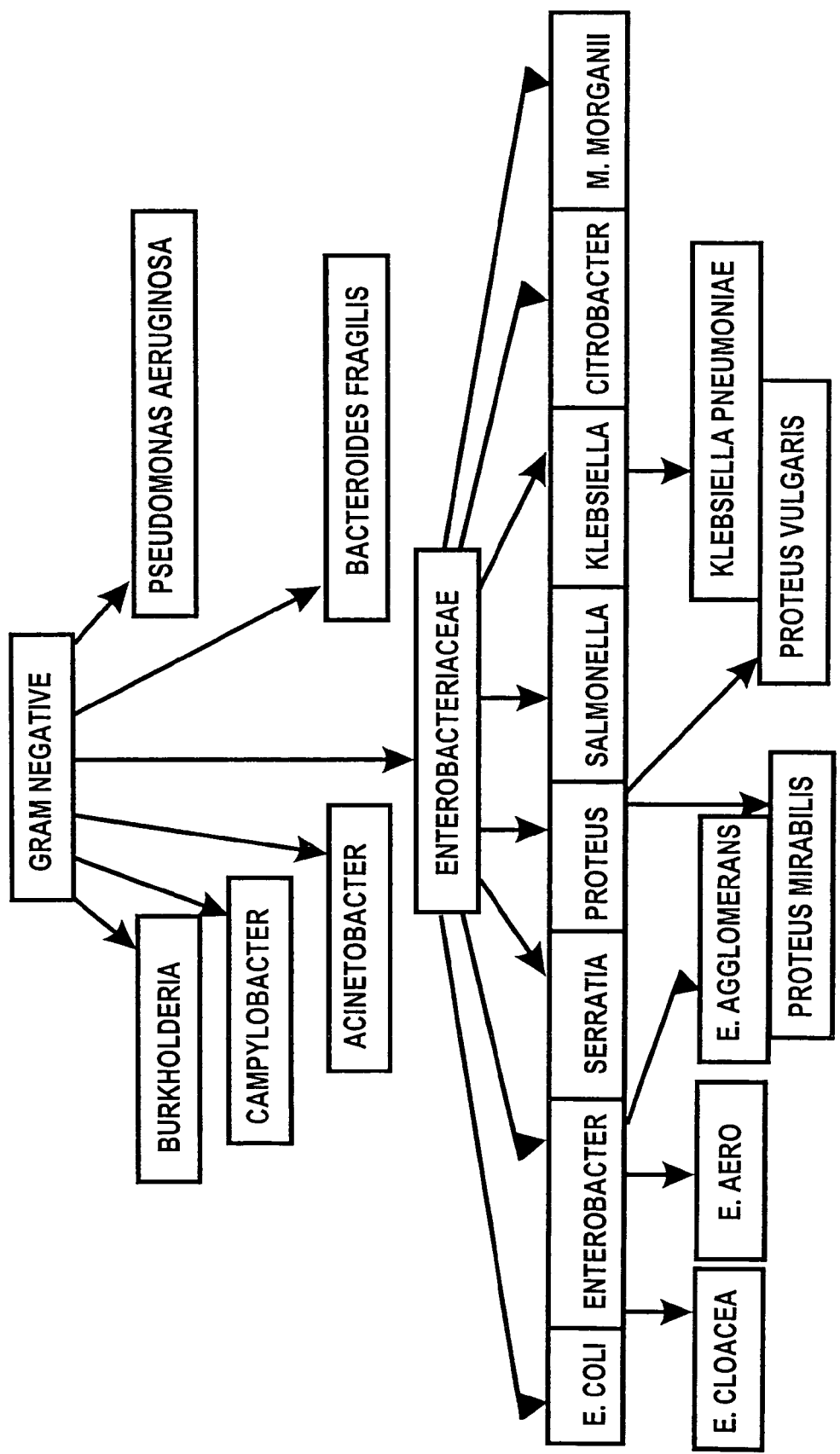
FIG. 3 is a schematic diagram showing the phylogenetic hierarchy among the Gram$^{(-)}$ bacteria. Several species of Gram$^{(-)}$ bacteria are shown as being related to the Enteric (Enterobacteriaceae) bacteria. Arrows indicate phylogenetic relationships.

Arrows appearing in each of FIGS. 1-3 indicate phylogenetic relationships and establish pathways for identifying microorganisms. For example, FIG. 2 shows that *S. aureus* is a bacterium that is a member of the *Staphylococcus* genus, and is classified as a member of the Low (G+C) sub-category of $Gram^{(+)}$ bacteria. Thus, rRNA from *S. aureus* would be expected to hybridize with: a pan-bacterial probe, a probe for $Gram^{(+)}$ bacteria, a probe specific for the *Staphylococcus* genus and a species-specific probe for *S. aureus*. Since this bacterium is a member of the Low (G+C) subset of $Gram^{(+)}$ bacteria, no hybridization is expected with a probe specific for the High (G+C) subset of $Gram^{(+)}$ bacteria. Accordingly, the relationships set forth in FIGS. 1-3 can be used for predicting profiles of positive and negative hybridization for ribosomal nucleic acids at various addresses in a probe matrix.

Thus, one aspect of the present invention relates to methods of identifying microbes wherein collections of addresses that comprise hybridization probes having binding specificity for ribosomal nucleic acid target sequences distinguish organisms based on molecular phylogeny. Particularly preferred probes that can be used in the method can: (1) distinguish bacteria from fungi, (2) distinguish $Gram^{(+)}$ bacteria from $Gram^{(-)}$ bacteria, (3) identify the High (G+C) subset of $Gram^{(+)}$ bacteria, (4) identify bacteria that are members of the family Enterobacteriaceae, (5) identify bacteria that are grouped as *Enterococcus*, (6) identify bacteria that are members of the *Staphylococcus* genus, (7) identify bacteria that are members of the *Campylobacter* group, and (8) make species-level identifications of *E. coli, Staphylococcus aureus, Candida albicans, Pseudomonas aeruginosa* and *Streptococcus pneumoniae*. It is to be understood that a positive identification of a microorganism at the species-level is indicated by a positive hybridization result with a species-specific probe. This is also true for the positive identification of microorganisms as $Gram^{(+)}$ bacteria. However, $Gram^{(-)}$ bacteria are identified as the subset of bacteria having ribosomal nucleic acids that fail to hybridize a probe specific for $Gram^{(+)}$ bacteria. This subtractive approach to identifying $Gram^{(-)}$ bacteria is both simple and highly convenient because the $Gram^{(-)}$ bacteria are somewhat more divergent than the $Gram^{(+)}$ bacteria. While it might be necessary to employ several different probes to identify a substantial fraction of the Gram$^{(-)}$ bacteria, Gram$^{(+)}$ bacteria can be identified using a single probe. Limiting the number of probes in a hybridization reaction usually reduces the possibility for undesired cross-hybridization. Nonetheless, a polynucleotide probe specific for Gram$^{(-)}$ bacteria can be used for distinguishing the ribosomal nucleic acids of Gram$^{(+)}$ bacteria from those of Gram$^{(-)}$ bacteria.

A preferred set of addresses useful for carrying out matrix-based classification of microorganisms includes: a pan-bacterial address; a pan-fungal address; an address for distinguishing Gram$^{(+)}$ and Gram$^{(-)}$ bacteria, and an address for identifying the Actinomycetes subset of Gram$^{(+)}$ bacteria. An address for bacteria in the family Enterobacteriaceae is further preferred for use in combination with the foregoing set of addresses because the additional information provided by this address is useful for categorizing Gram$^{(-)}$ bacteria. An address for bacteria in the genus *Enterococcus* similarly is useful for gaining insight into the identity of organisms falling under the category of Low (G+C), Gram$^{(+)}$ bacteria. Other useful addresses identify members of the *Staphylococcus* genus and the *Campylobacter* group of bacteria. Finally, species-level identifications using the matrix-based assay include: a species-specific address for *E. coli* (a Gram$^{(-)}$ bacterium that is a member of the family Enterobacteriaceae), a species-specific address for *Staphylococcus aureus* (a member of the Low (G+C) subset of Gram$^{(+)}$ bacteria that falls under the *Staphylococcus* genus), a species-specific address for *Candida albicans* (a fungus), a species-specific address for *Pseudomonas aeruginosa* (a Gram$^{(-)}$ bacterium) and a species-specific address for *Streptococcus pneumoniae* (a member of the Low (G+C) subset of Gram$^{(+)}$ bacteria). Each of these addresses can be represented by one or more polynucleotide probes disposed at a particular locus in a testing device such as any of those described herein.

Table 4 presents some of the highly preferred three-address probe matrices that include higher-order, intermediate-order and lower-order addresses. The entries in the Table specifically illustrate some of the particularly preferred combinations of addresses that can be used to create task-specific probe matrices. These matrices have their greatest utility in cases where the identity of an organism already had been defined in broad terms. More specifically, the probe matrices listed in Table 4 would be useful for further characterizing bacterial organisms (rows 1-7), and fungal organisms (row 8).

TABLE 4

Illustrative Three-Address Matrices

| Higher-Order Address | Intermediate-Order Address | Lower-Order Address |
| --- | --- | --- |
| pan-bacterial | Gram$^{(+)}$ | Actinomycetes |
| Gram$^{(+)}$ | Actinomycetes | probe for bacterial species detected at the Actinomycetes address |
| pan-bacterial | Gram$^{(+)}$ | probe for a bacterial species detected at the Gram$^{(+)}$ address |
| pan-bacterial | family Enterobacteriaceae | probe for bacterial species detected at the Enterobacteriaceae address |
| pan-bacterial | genus *Staphylococcus* | probe for bacterial species detected at the genus *Staphylococcus* address |
| pan-bacterial | genus *Enterococcus* | probe for bacterial species detected at the genus *Enterococcus* address |
| pan-bacterial | genus *Campylobacter* | probe for bacterial species detected at the genus *Campylobacter* address |
| pan-fungal | *Candida* group | probe for fungal species detected at the *Candida* group address |

A clinically important fraction of the Actinomycetes subset of Gram$^{(+)}$ bacteria includes the organisms: *Mycobacteria tuberculosis*, *Mycobacteria bovis*, *Mycobacteria bovis* BCG and *Mycobacteria africanum* which make up the *Mycobacterium tuberculosis* complex (TB Complex). This classification is specifically illustrated in FIG. 2. Organisms of the TB Complex are responsible for significant morbidity and mortality in humans. *M. tuberculosis* is the most common TB Complex pathogen isolated from humans. *M. bovis* BCG may be transmitted from infected animals to humans. *M. africanum* causes pulmonary tuberculosis in tropical Africa. U.S. Pat. No. 5,906,917, the disclosure of which is hereby incorporated by reference, instructs two highly specific hybridization probes useful for identifying the TB Complex. The first probe has the sequence GGTAGCGCTGAGACATATC-CTCC (SEQ ID NO:42), and can be used in conjunction with helper oligonucleotides having the sequences CCGCTAAC-CACGACACTTTCTGTACTGCCTCTCAGCCG (SEQ ID NO:43) and CACAACCCCGCACACACAACCCCTAC-CCGGTTACCC (SEQ ID NO:44). The second probe has the sequence CAGAACTCCACACCCCCGAAG (SEQ ID NO:45), and can be used in conjunction with helper oligonucleotides having the sequences TGATTCGT-CACGGGCGCCCACACACGGGTACGG-GAATATCAACCC (SEQ ID NO:46) and CTACTACCAGCCGAAGTTCCCACGCAGCCC (SEQ ID NO:47) and GGAGTTGATCGATCCGGTTTTGGGTGGT-TAGTACCGC (SEQ ID NO:48) and GGGGTACGGGC-CGTGTGTGTGCTCGCTAGAGGCTTTTCTTGGC (SEQ ID NO:49). These probes are highly preferred for identifying subsets of Actinomycetes bacteria in probe matrices. More-particularly, highly preferred probe matrices would include addresses for Gram$^{(+)}$ bacteria, Actinomycetes and the TB Complex. Other highly preferred probe matrices would include addresses for pan-bacterial organisms, Gram$^{(+)}$ bacteria and the TB Complex. The TB Complex address allows identification of a subset of organisms that can produce positive hybridization signals at higher-order addresses, such as pan-bacterial, Gram$^{(+)}$ and Actinomycetes addresses.

*Listeria monocytogenes* is a Gram$^{(+)}$ bacterium that is not a member of the Actinomycetes. This organism is primarily a soil-borne bacterium that is dispersed throughout the environment. This organism, which has been found in water sources, agricultural products and animals, has been recognized as a human pathogen for more than 50 years. It is the etiologic agent of listeriosis, causing meningitis, encephalitis, septicemia and endocarditis in humans. U.S. Pat. No. 6,028,187, the disclosure of which is hereby incorporated by reference, instructs a highly specific hybridization probe that can be used for hybridizing the ribosomal nucleic acids of *Listeria monocytogenes*. This probe has the sequence CTGAGAATAGTTTTATGGGATTAGCTCC (SEQ ID NO:50), and can be used in conjunction with a helper oligonucleotide having the sequence GGCGAGTTGCAGCCTA- CAATCCGAA (SEQ ID NO:51). This probe is useful for identifying subsets of Gram$^{(+)}$ bacteria in probe matrices. Highly preferred probe matrices useful for performing hybridization procedures include addresses for Gram$^{(+)}$ bacteria and *Listeria monocytogenes*. Other highly preferred probe matrices include addresses for pan-bacterial organisms, Gram$^{(+)}$ bacteria and *Listeria monocytogenes*. The *Listeria monocytogenes* address allows identification of a subset of organisms that produce positive hybridization signals at higher-order addresses, such as pan-bacterial and Gram$^{(+)}$ addresses.

Other preferred lower-order addresses that can be used in conjunction with higher-order and intermediate-order addresses, such as the pan-bacterial address and the Gram$^{(+)}$ address, include an address for *Staphylococcus aureus* and an address for *Streptococcus pneumoniae*.

An *E. coli* address can be used as a lower-order address in combination with addresses for pan-bacterial organisms and an address for bacteria in the family Enterobacteriaceae.

A *Staphylococcus aureus* address can be used as a lower-order address in combination with addresses for pan-bacterial organisms and an address for bacteria in the genus *Staphylococcus*.

Preferred addresses that can be added to any of the above-described three-address matrices include an address for identifying pan-fungal organisms and an address for identifying particular species of fungal organisms, such as *Candida albicans*.

In addition to the probes for identifying pan-fungal organisms and the yeast species *Candida albicans*, another probe is highly preferred as a component of probe matrices that can be used for classifying fingi. More specifically, certain highly preferred probe matrices include polynucleotide probes that specifically hybridizes ribosomal nucleic acids from a plurality of *Candida* species, including *C. albicans, C. tropicalis, C. dubliniensis, C. viswanathii* and *C. parapsilosis*, without hybridizing other species such as *C. krusei* or *C. glabrata*. This hybridization specificity is provided by a probe having the sequence GCGTCAATAAAAGAACAACAAC-CGATCCC (SEQ ID NO:55). This probe can be used in conjunction with helper oligonucleotides having the sequences

```
                                        (SEQ ID NO:56)
TAGTCGGCATAGTTTATGGTTAAGAC (OMeT)
and (SEQ ID NO:57)
CCCAGAACCCAAAGACTTTGATTTCTCGTAAGGTGCCGATT.
```

These polynucleotides are highly preferred as components in probe matrices having an address that specifically hybridize ribosomal nucleic acids from *C. albicans, C. tropicalis, C. dubliniensis, C. viswanathii* and *C. parapsilosis*. Notably, this address would be considered to be an intermediate-order address with respect to the combination of a pan-fungal address and an address that identified *C. albicans*. Thus, a highly preferred three-address probe matrix that conforms with the requirements and guidelines described herein includes: (1) a pan-fungal address that hybridizes ribosomal nucleic acids from a plurality of fungal species but not bacterial species, (2) a *Candida* group address that hybridizes ribosomal nucleic acids from a plurality of *Candida* species, including *C. albicans, C. tropicalis, C. dubliniensis, C. viswanathii* and *C. parapsilosis*, and (3) a *Candida albicans* address that specifically hybridizes ribosomal nucleic acids from *Candida albicans*.

Alternative hybridization probes can be used as a component of probe matrices for specifically identifying *Candida albicans* ribosomal nucleic acids. For example, a probe having the sequence CGGCCATAAAGACCTACCAAGCG (SEQ ID NO:52) can be used in conjunction with helper oligonucleotides having the sequences CCAGTTCTAAGT-TGATCGTTAAACGTGCCCCGGA (SEQ ID NO:53) and TGTCTACAGCAGCATCCACCAGCAGTCCGTCGTG (SEQ ID NO:54) for hybridizing ribosomal nucleic acids of numerous *C. albicans* strains and *C. dubliniensis* without substantially hybridizing ribosomal nucleic acids of *C. tropicalis, C. viswanathii, C. glabrata, C. krusei* or *C. parapsilosis*. These polynucleotides are highly preferred as components in probe matrices which include an address that specifically identifies *C. albicans* and *C. dubliniensis*.

A particularly useful classification system that takes advantage of phylogenetic differences among bacteria was developed to allow identification of non-pathogenic Staphylococcal bacteria. A *Staphylococcus* genus probe was first used to identify organisms as members of the broad genus of Staphylococcal bacteria. A species-specific probe was used independently to identify *Staphylococcus aureus*. Armed with knowledge about the hybridization profile of these two probes, it is possible to identify a group of bacteria referred to herein as "Staph-Not-Aureus" (SNA), a clinically relevant identification of bacteria that are one of the most common causes of false-positive blood cultures. While *Staphylococcus aureus* is considered a "true pathogen" when detected in blood culture, Staphylococcal bacteria that are of a species different from *S. aureus* are generally considered to represent contaminating skin bacteria that were inadvertently collected during the blood draw.

Thus, highly useful information about the identity of Staphylococcal bacteria can be derived by determining whether bacteria having ribosomal nucleic acids that hybridize a probe specific for the *Staphylococcus* genus also hybridizes a *S. aureus* species-specific probe. Any bacterium having rRNA or rDNA that hybridizes the *Staphylococcus* genus probe but not the *S. aureus* species-specific probe is classified as SNA. If a blood culture bottle contains SNA bacteria, that finding will indicate the culture is likely to be a false-positive culture that was inoculated with bacteria from a skin surface that was not adequately free of microorganisms at the time that blood was drawn from the donor. This represents a simple example for how a collection of hybridization probes having specificity for molecular phylogenetic branch-points can be used to identify microorganisms as members of a genus or species.

Alternative methods of distinguishing between pathogenic *S. aureus* and harmless *Staphylococcus* bacteria from the skin involve conducting a standard coagulation test. Whereas most cultures of *S. aureus* coagulate, cultures of harmless Staphylococcal bacteria usually do not exhibit this characteristic. These harmless Staphylococcal bacteria that fail to coagulate are referred to as "coagulase-negative Staph" or "CONS." The ability to show a positive coagulase test also varies between commercial tests for the same bacterial species. Thus, the method of identifying microorganisms described herein advantageously can include a step for identifying CONS as the subset of *Staphylococcus* bacteria that do not hybridize a *S. aureus* species-specific hybridization probe.

A probe matrix for detecting non-aureus *Staphylococcus* ribosomal nucleic acids includes an address for detecting bacteria that are members of the genus *Staphylococcus*, and an address for detecting the species *S. aureus*. An address for hybridizing ribosomal nucleic acids of pan-bacterial organisms optionally can be included for convenience. Positive hybridization results at the pan-bacterial address, the *Staphy-*

*lococcus* genus address and the *S. aureus* address would indicate the presence of *S. aureus* in the test sample. Conversely, the presence of non-aureus *Staphylococcus* bacteria ("SNA") would be indicated by positive hybridization results at the pan-bacterial address and the *Staphylococcus* genus address, but a negative result at the *S. aureus* address. Of course, the utility of this matrix could be expanded by further including addresses for pan-fungal organisms, and for the species *Candida albicans*. Indeed, a highly preferred probe matrix includes: (1) a pan-bacterial address, (2) an address for bacteria falling under the *Staphylococcus* genus, (3) an address for the species *Staphylococcus aureus*, and (4) an address for pan-fungal organisms. An additional address for the species *Candida albicans* optionally can be included. In an even more highly preferred probe matrix, some of these addresses are combined at one or more common loci. This latter aspect of the invention is referred to as "hybridization probe multiplexing."

Hybridization Probe Multiplexing

Another feature of the invention relates to the "multiplexing" aspect of probe hybridization procedures. Multiplexing refers to a plurality of nucleic acid probes that are physically combined at a single locus in a testing device so that a qualitatively positive hybridization signal at the locus indicates that one of the probes hybridized to a target without indicating which of the plurality of probes hybridized. Since a single locus in a testing device can accommodate a plurality of polynucleotide hybridization probes that can be used for indicating the presence or absence of one or more ribosomal nucleic acid sequences, both the physical locus and the types of microorganism identified by a positive hybridization signal at the locus is referred to herein as an "address."

During the development of the invention it was discovered that some of the nucleic acid probes conveniently could be combined in the same hybridization reaction and would yield results useful for determining whether one or more different types of microorganism was present in a biological sample. For example, probes specific for bacteria in the family Enterobacteriaceae and bacteria in the genus *Enterococcus* can be combined at a first common locus because the uniqueness of the hybridization profile for all microorganisms to be identified in the probe matrix is not compromised by this combination. Similarly, probes specific for bacteria falling under the *Staphylococcus* genus and under the *Campylobacter* group can be combined at a second common locus without compromising the uniqueness of hybridization profiles. Advantageously, when a probe matrix includes a plurality of addresses that serve as unique pathways for identifying different microorganisms, it becomes possible to detect and resolve mixed cultures of microorganisms.

Since negative hybridization results are meaningful in the context of a probe matrix hybridization procedure, certain addresses can be combined at common loci without compromising the ability to extract highly useful information from the hybridization results. This point can be illustrated by considering a probe matrix that includes: (a) a pan-bacterial address, (b) an address for detecting Gram$^{(+)}$ bacteria, (c) an address for the bacterial species *Staphylococcus aureus*, (d) an address for pan-fungal organisms, and (e) an address for the fungal species *Candida albicans*. Without compromising the integrity of information that can be derived from hybridization results, the matrix can be configured in the following way using four loci: (1) pan-bacterial address, (2) pan-fungal address, (3) Gram$^{(+)}$ address, and (4) species addresses for *S. aureus* and *C. albicans*. In this example the two species addresses can be combined because a positive hybridization result at the common locus necessarily must be accompanied by positive results at either (1) the pan-bacterial address and the Gram$^{(+)}$ address, or (2) the pan-fungal address. The former hybridization result, taken in combination with a positive hybridization result at the species address, would indicate the test organism was the bacterium *S. aureus*. Conversely, the latter hybridization result would indicate the organism was the yeast *C. albicans*. This illustrates how the species origin of a ribosomal nucleic acid can be determined from a positive hybridization result at a single address that identifies more than one species of organism.

Indeed, it is also preferable when using complex matrices to combine a collection of species-specific probes at a single address in the matrix. A preferred collection of species probes would, for example, include probes having specificity for the rRNA of *E. coli, Staphylococcus aureus, Candida albicans, Pseudomonas aeruginosa* and *Streptococcus pneumoniae*. Again, a positive hybridization result at a matrix address corresponding to this collection of species probes would be easily resolved by considering results at other addresses in the matrix. However, it is important that the nucleic acids hybridized by the species-specific probes that are disposed at a single address in the probe matrix must be distinguishable from each other by identifying information provided by at least one other address in the probe matrix. Thus, an address corresponding to a collection of probes having specificity for different microbial species must each correspond to a unique pattern of higher-order relationships among the other addresses. The profiles of positive and negative hybridization results at the various addresses in the probe matrix can be easily resolved using a "look-up table."

Determining which probes can be combined at the same locus in a matrix-based hybridization reaction is a matter of routine practice. Indeed, based on known molecular phylogenetic relationships readily ascertainable from the scientific literature, any bacterium of interest can be assigned a profile of expected positive- and negative-hybridization results for each of a collection of addresses in a particular matrix. Each microorganism species corresponding to a species-specific hybridization probe in the matrix must be identifiable by a unique profile of positive and negative hybridization results in order to identify those species unambiguously.

Apart from certain probes that are preferably employed in hybridizations conducted at physically distinct loci, remaining probes in the matrix can be mixed in any combination subject to the provision that probes are not combined at the same locus if such a combination results in a matrix wherein two different species-specific probes will be characterized by a common hybridization profile. For example, in a probe matrix having addresses for pan-bacterial organisms, Gram$^{(+)}$ bacteria, the Actinomycetes subset of Gram$^{(+)}$ bacteria, and the *Staphylococcus* genus, it would not be acceptable to have a single address representing species-specific probes for both *Staphylococcus aureus* and *Staphylococcus epidermidis* because the hybridization profiles for these two species in the matrix would be indistinguishable. Thus, if a species-level identification is desired, probes can be combined at a common address as long as the profile of positive and negative hybridization results corresponding to each species identification is distinguishable from all other profiles in the matrix. The same is true for higher-order phylogenetic groupings, including genus-level groupings.

It is to be noted that, unless distinguishable labels are used for hybridization probes that detect nucleic acids from different species of organism, a positive hybridization signal at an address corresponding to multiple species probes may not unambiguously identify which of the species probes is responsible for the hybridization. In such an instance, resolution down to the level of a hybridizing probe will depend on interpretation of the result in the context of other results at different addresses in the probe matrix.

Finally, the multiplex hybridization approach described herein provides even further advantages because the complexity of instrumentation needed to perform the assay is minimized. More particularly, the invented method does not require elaborate laboratory apparatus for carrying out the protocol or for reading the assay results. The procedure fits into the standard clinical algorithm and device platform, and so does not require expensive equipment that is dedicated to the assay. Thus, no special instrumentation platform is required for performing the probe matrix hybridization procedures described herein.

Specific Example of Hybridization Probe Multiplexing

Multiplexing in probe matrices provides a means for extracting proportionately large amounts of hybridization data from a relatively small number of loci. An example of a useful probe matrix employing the above-described addresses in a multiplexed configuration with four loci has the following structure:

| Locus | Address |
|---|---|
| 1 | Pan-bacterial |
| 2 | Pan-fungal |
| 3 | Gram[(+)] and *Candida* group (*C. albicans*/*C. tropicalis*/*C. dubliniensis*/*C. viswanathii*/*C. parapsilosis*) |
| 4 | *Staphylococcus aureus* and *Candida albicans* |

Since any uni-microbial biological sample would not simultaneously contain both bacterial and fungal organisms, it follows that either the bacterial or fungal intermediate-order and lower-order addresses at the third and fourth loci can be exchanged to give a matrix having the following structure:

| Locus | Address |
|---|---|
| 1 | Pan-bacterial |
| 2 | Pan-fungal |
| 3 | Gram[(+)] and *Candida albicans* |
| 4 | *Staphylococcus aureus* and *Candida* group (*C. albicans*/*C. tropicalis*/*C. dubliniensis*/*C. viswanathii*/*C. parapsilosis*) |

These two examples of multiplexed hybridization probes describe preferred probe matrices in accordance with the present invention. These matrices include three addresses specific for ribosomal nucleic acids of bacterial organisms and three addresses specific for ribosomal nucleic acids of fungal organisms. The addresses for each of the bacterial and fungal divisions are related to each other as higher-order, intermediate-order and lower-order addresses. These matrices also illustrate particular examples wherein higher-order addresses for organisms belonging to different superkingdoms are combined into the same probe matrix. Finally, multiplexing of the addresses in these matrices allows the configuration of a device having six addresses at only four loci.

Chemical Structure of Oligonucleotides

Oligonucleotides useful for performing probe matrix hybridization procedures may be modified with chemical groups to enhance their performance. Thus, it is to be understood that references to "oligonucleotide probes" or "helper oligonucleotides" or simply "oligonucleotides" or "probes" embrace polymers of native nucleotides as well as polymers that include at least one nucleotide analog.

Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or to nuclease enzymes. Other analogs that can be incorporated into the structures of the oligonucleotides disclosed herein include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. The PNAs are able to bind complementary ssDNA and RNA strands. Methods for making and using PNAs are disclosed in U.S. Pat. No. 5,539,082. Another type of modification that can be used to make oligonucleotides having the sequences described herein involves the use of non-nucleotide linkers (e.g., Arnold, et al., "Non-Nucleotide Linking Reagents for Nucleotide Probes", U.S. Pat. No. 6,031,091 hereby incorporated by reference) incorporated between nucleotides in the nucleic acid chain which do not interfere with hybridization or the elongation of a primer.

Examples of Useful Polynucleotide Probes

Polynucleotide probes useful for identifying microbes according to the methods described herein typically will hybridize rRNA or rDNA of particular groups or species of microorganism with high specificity. For example, a "pan-bacterial" probe that specifically hybridizes the rRNA of all or nearly all known bacterial species without hybridizing fungal organisms can be used to determine whether a biological sample contains bacteria. Similarly, a "pan-fungal" probe that specifically hybridizes the rRNA of all or nearly all known fungal species without hybridizing bacterial rRNA is useful for determining that a rRNA sample contains fungi. Table 5 presents polynucleotide sequences of probes that have been used to illustrate the invention. Of course, those having an ordinary level of skill in the art will realize that other probes can be substituted for the probes that are presented in the Table.

TABLE 5

Illustrative Probe and Helper Oligonucleotide Sequences

| Target rRNA | Function | Sequence |
|---|---|---|
| pan-bacterial | probe | CGACAAGGAATTTCGC (SEQ ID NO:1) |
| | helper | TACCTTAGGACCGTTAT (SEQ ID NO:2) |
| | helper | CAGGTCGGAACTTACC (SEQ ID NO:3) |

TABLE 5-continued

Illustrative Probe and Helper Oligonucleotide Sequences

| Target rRNA | Function | Sequence |
|---|---|---|
| pan-fungal | probe | GTCTGGACCTGGTGAGTTTCCC (SEQ ID NO:4) |
|  | helper | CGTGTTGAGTCAAATTAAGCCGC (SEQ ID NO:5) |
|  | helper | GCTCTCAATCTGTCAATCCTTATTGT (SEQ ID NO:6) |
| Gram(+) | probe | GAGGGAACCTTTGGGCGC (SEQ ID NO:7) |
|  | helper | CTCCGTTACCTTTTAGGAGGCGACCGCCC (SEQ ID NO:8) |
|  | helper | CTCCGTTACATTTTAGGAGGC (SEQ ID NO:9) |
| High (G + C) subset of Gram(+) bacteria (*Actinomycetes*) | probe | CGAGCATCTTTACTCGTAGTGCAATTTCG (SEQ ID NO:10) |
|  | helper | CCGAGTCTGTGGTTGAGACAGTGGG (SEQ ID NO:11) |
|  | helper | GGTCTTTCCGTCCTGCCGCGCGTAA (SEQ ID NO:12) |
| Enterobacteriaceae (Enteric bacteria) | probe | CCGCTTGCTCTCGCGAG (SEQ ID NO:13) |
|  | helper | GTCGCTTCTCTTTGTATGCGCCATTGTAGCACGTGTGTAGC (SEQ ID NO:14) |
|  | helper | GGACTACGACGCACTTTATGAGGT (SEQ ID NO:15) |
| *Enterococcus* spp | probe | CTCCTAGGTGCCAGTCAAATTTTG (SEQ ID NO:16) |
|  | helper | TCTACGGGGCTTTTACCCTTTCTAGCAGACC (SEQ ID NO:17) |
|  | helper | CCTCGTGTTCCGCCGTACTCAGGATC (SEQ ID NO:18) |
| *Enterococcus* spp | probe | CATCATTCTCAATTCCGAGGC (SEQ ID NO:19) |
|  | helper | TAGCCCTAAAGCTATTTCGGAGAGAACCAGCTATCTCC (SEQ ID NO:20) |
|  | helper | CCCTAGTCCAAACAGTGCTCTACCTC (SEQ ID NO:21) |
| *Staphylococcus* Genus | probe | CCGAACTGAGAACAACTTTATGGGATTTGC (SEQ ID NO:22) |
|  | helper | TTGACCTCGCGGTTTCG (SEQ ID NO:23) |
|  | helper | GCGATTCCAGCTTCATGTAGTCGAGTTGCAGACTACAAT (SEQ ID NO:24) |
| *Campylobacter* spp | probe | GGTTCTTAGGATATCAAGCCCAGG (SEQ ID NO:25) |
|  | helper | GTCTCTAAGTTCTAGCAAGCTAGCACCCTCATATCTCTA (SEQ ID NO:26) |
| *E. coli* | probe | GGGTAACGTCAATGAGCAAAGGTATTAAC (SEQ ID NO:27) |
|  | helper | TTTACTCCCTTCCTCCCCGCTGAAAGTACTTTACAACCCG (SEQ ID NO:28) |
|  | helper | CACGGAGTTAGCCGGTGCTTCTTCTGC (SEQ ID NO:29) |
| *Streptococcus pneumoniae* | probe | CAAAGCCTACTATGGTTAAGCC (SEQ ID NO:30) |
|  | helper | ACAGCCTTTAACTTCAGACTTATCTAACCGCCTGCGC (SEQ ID NO:31) |
|  | helper | TCTCCCCTCTTGCACTCAAGTTAAACAGTTTC (SEQ ID NO:32) |
| *Pseudomonas aeruginosa* | probe | CCCAGAGTGATACATGAGGCG (SEQ ID NO:33) |
|  | helper | CCCTAGCCGAAACAGTTGCTCTACCC (SEQ ID NO:34) |
|  | helper | CTACCTAAATAGCTTTCGAGGAGAACCAGCTATCTC (SEQ ID NO:35) |
| *Candida albicans* | probe | GCTGGCCTGAAAAATCAAGCACG (SEQ ID NO:36) |
|  | helper | TTGAAACGGAGCTTCCCCATCTCTTAGGATCGACTAACCC (SEQ ID NO:37) |
|  | helper | CCAAGTTCCGGAATTTTAACCGGATTCCCTTTCGATG (SEQ ID NO:38) |
| *Staphylococcus aureus* | probe | CCACTCAAGAGAGACAACATTTTCGACTAC (SEQ ID NO:39) |
|  | helper | GATGATTCGTCTAATGTCGACCTTTGTAACTCC (SEQ ID NO:40) |
|  | helper | CGGAATTTCACGTGCTCCGTCGTACTCAGGAT (SEQ ID NO:41) |

The probes and helpers shown in Table 5 specifically hybridized the corresponding target rRNAs cited in the Table, and so identified the collection of organisms listed above in connection with the illustrative taxonomic differentiators.

While the invented devices and methods have been illustrated using particular oligonucleotide probes, it is to be understood that other nucleic acid probes can be substituted with equally good results. For example, Hogan et al., in U.S. Pat. No. 5,541,308, hereby incorporated by reference, teach a collection of oligonucleotide probes that can be used in hybridization assays to detect a broad phylogenetic cross-section of bacteria. This collection of probes could be employed at a pan-bacterial address in an alternative probe matrix. An alternative hybridization probe that has been used in probe matrices at an address for detecting ribosomal nucleic acids of pan-bacterial organisms has the sequence GGAACTTACCCGACAAGGAATTTCGCTACCTTAGG (SEQ ID NO:58) and can be used in conjunction with helper oligonucleotides having the sequences ACCGTTATAGT-TACGGCCGCCGTTTACCGGGGCTTC (SEQ ID NO:59), GCCTGGCCATCATTACGCCATTCGTGCAGGTC (SEQ ID NO:60) and GCCCAAATCGTTACGCCTTTCGT-GCGGGTC (SEQ ID NO:61). These polynucleotides are highly preferred as components in probe matrices having an address that identifies pan-bacterial organisms, and can be substituted for the pan-bacterial probe described in the working Examples with equally good results. U.S. Pat. No. 5,541,308 further teaches oligonucleotide probes that are reactive with the rRNA of numerous fungal organisms. Similarly, Weisburg et al., in U.S. Pat. No. 5,403,710, hereby incorporated by reference, disclose two "pan-generic" probes that hybridize nucleic acids from most fungi. Either of these latter sets of probes could be employed at a pan-fungal address in an alternative probe matrix. U.S. Pat. No. 5,635,348, hereby incorporated by reference, discloses the sequences of probes useful for identifying Gram[(+)] and Gram[(−)] bacteria. Oligonucleotide hybridization probes useful for identifying the High (G+C) subset of Gram[(+)] bacteria are disclosed by Roller et al., in *J Gen Micro* 138:1167 (1992) and in *Microbiology* 140:2849 (1994). Sheiness et al., in U.S. Pat. No. 5,776,694, hereby incorporated by reference, teach a probe having specificity for Enterobacteriaceae. Hogan et al., in U.S. Pat. No. 5,674,684, hereby incorporated by reference, disclose hybridization probes having binding specificity for the rRNAs of *Enterococci*, and disclose and claim alternative hybridization probes having binding specificity for the rRNAs of *Campylobacters*. Thus, those having an ordinary level of skill in the art will appreciate that nucleic acid probes other than those particularly described in Table 5 can be used for carrying out the matrix-based hybridization methods disclosed herein.

As indicated in the preceding Table, several different species-specific probes can be used to carry out a probe matrix hybridization procedure. For the purpose of illustrating the invention, species-specific probes were used for identifying *E. coli, Staphylococcus aureus, Candida albicans, Pseudomonas aeruginosa* and *Streptococcus pneumoniae*. It will be clear to those having ordinary skill in the art that additional species-specific probes can be added or substituted for the set employed in the Examples detailed herein. Of course, the selection of species-specific probes is subject to the provision that the profile of positive and negative hybridization results at the various addresses in the matrix are unique for each species-specific probe. Two microorganisms represented by different species-specific probes should not have identical hybridization profiles at all other addresses in the matrix if a species-level identification is desired.

Useful Polynucleotide Labeling, Hybridization and Detection Systems

Essentially any labeling and detection system that can be used for monitoring specific nucleic acid hybridization can be used in conjunction with the probe matrices disclosed herein. Included among the collection of useful labels are: radiolabels, enzymes, haptens, linked oligonucleotides, chemiluminescent molecules and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

It should be apparent that probe matrices prepared according to the methods described herein will have non-random sequences that were selected using analytical techniques based on molecular phylogenetic analysis. Probes of the invention preferably will have lengths of from 14 to 45 nucleotides, or more preferably between 16 and 30 nucleotides, but can be as long as 100 nucleotides in length. Helper oligonucleotides preferably will have similar lengths. The fact that the invented probe matrices have non-random sequences contrasts with the short, random oligonucleotide sequences disposed in high density arrays on "DNA microchips" of the sort used for conducting gene expression studies (*Science* 282: 396 (1998)).

High stringency conditions useful for conducting the hybridization procedures disclosed herein include conditions of 55-65° C. when the salt concentration is in the range of 0.6-0.9 M. Preferred salts include lithium chloride, but other salts such as sodium chloride and sodium citrate also can be used in the hybridization solution. Other useful high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. It is preferred that all of the probes used in a probe matrix have Tm values that are within 15° C. of each other. It is further preferred that all of the probes used in a probe matrix optimized for hybridization at about 60° C. will have Tm values in the range of from 63° C. to about 78° C.

Notably, methods suitable for liberating from microorganisms the nucleic acids that can be subjected to the hybridization methods disclosed herein have been described by Clark et al., in U.S. Pat. No. 5,837,452 and by Kacian et al., in U.S. Pat. No. 5,5,364,763. The disclosures of these patents are hereby incorporated by reference.

Apparatus Useful for Conducting Hybridization Reactions

The matrix-based method of identifying microorganisms can be carried out using any of several different types of testing formats. Examples of formats that can be used to conduct the hybridization include, but are by no means limited to: individual tubes where one or more probes can be physically isolated from other probes or collections of probes contained in different tubes; the wells of a 96-well or other multi-well microtiter plate; and a solid support such as a dipstick or a "DNA chip" where polynucleotide probes are immobilized to the support at different addresses in a spaced-apart configuration.

Identifying microorganisms by the invented nucleic acid testing system advantageously can be performed without requiring any in vitro amplification step. Alternative microorganism identification systems that employ a preliminary amplification step, for example using the polymerase chain reaction (PCR), are believed to be susceptible to false-positive results arising from environmental contamination. These false-positive results can arise because of improper clinical laboratory sampling techniques, carry-over contamination from amplification reactions having high amplicon levels or from contamination of laboratory reagents used for specimen processing or nucleic acid amplification. All of these difficulties can be avoided when polynucleotides from a biological sample are subjected to the probe matrix hybridization procedure without first undergoing an in vitro amplification step.

According to one approach for conducting matrix-based hybridization procedures, probes can be labeled with distinguishable labels. Examples of particularly preferred chemiluminescent labels that can be used for performing the methods described herein are the acridinium ester (AE) labels disclosed by Woodhead et al., in U.S. Pat. No. 5,756,011, the disclosure of which is hereby incorporated by reference. More particularly, a single address may include distinct probes that are independently labeled with chemiluminescent labels that emit peak energy at different times after generating a light emission. Materials and methods that can be used for making and using distinguishable probes useful in connection with the present invention can be found in U.S. Pat. No. 5,756,011, the disclosure of which is hereby incorporated by reference. Fluorescent labels that produce light at different wavelengths following excitation represent still other examples of distinguishable labels that can be used in connection with the procedures described herein. In this way, two probes that employ distinguishable labels can be distinguished from each other even though they are combined at the same locus of a testing device. Accordingly, it is possible to combine large numbers of different probes at a single address while still being able to distinguish the results of hybridization for the different probes or sets of probes.

Kits for Conducting Probe Matrix Hybridization Procedures

The materials used for carrying out probe matrix hybridization procedures may be incorporated into kits that can be used for conducting diagnostic procedures. The kits will include at least one device containing a plurality of probes for hybridizing nucleic acids from test organisms, and instructions for conducting a nucleic acid hybridization procedure using the device. The device will include a plurality of higher-order and lower-order addresses, essentially as disclosed herein, for hybridizing ribosomal nucleic acids of microorganisms undergoing testing. These addresses can correspond to the addresses particularly disclosed herein, but also may include different addresses as long as the relationship between higher-, intermediate-, and lower-order addresses is preserved. The kits optionally may contain instructions for detecting specific hybrids between probes that comprise the various addresses and target ribosomal nucleic acids obtained from biological samples that undergo testing with the device. The instructions can be either printed instructions or instructions stored on a computer-readable medium, such as a magnetic or optical disk.

Analytical Devices for Interpreting Hybridization Results

Results from probe matrix hybridization procedures can be interpreted or analyzed manually or with the aid of a computer or data processor ("processor"). Results from the hybridization procedure can be inputted into the processor through a user interface such as a keyboard, or inputted directly from an automated device such as a plate reader, film scanner or luminometer through a machine interface. The processor can then sort the positive and negative hybridization results to establish a profile. This profile is then compared with a look-up table stored in a memory device linked to the computer. The look-up table associates different profiles of hybridization results with different microorganism identities. In this way a hybridization profile determined using the probe matrix can be associated with the identity, or candidate identity in the case of ambiguous results that are characteristic of more than one organism, of the organism that was the source of nucleic acids used to conduct the hybridization procedure.

As indicated, automated devices useful for analyzing the results from probe matrix hybridization procedures will include a memory device having stored therein a look-up table which correlates the identities of microorganisms with positive and negative hybridization results at a number of different addresses in a probe matrix. Addresses that are particularly useful in the practice of the invention include: (a) an address that detects the ribosomal nucleic acids of pan-bacterial organisms but not pan-fungal organisms; (b) an address that detects the ribosomal nucleic acids from pan-fungal organisms but not pan-bacterial organisms; (c) an address that distinguishes the ribosomal nucleic acids of Gram$^{(+)}$ bacteria and the ribosomal nucleic acids of Gram$^{(-)}$ bacteria; and (d) an address that detects ribosomal nucleic acids from the Actinomycetes subset of Gram$^{(+)}$ bacteria. Typical memory devices include hard drives and floppy disks that comprise magnetic storage media. One automated device that has been used for interpreting the results of probe matrix hybridization procedures employed a computer internal hard drive as the memory device which served as the repository for the look-up table.

It is to be understood that a positive hybridization result at a particular address in a probe matrix does not necessarily indicate that the target nucleic acid contains precisely the complement of the sequence that was used as a probe. For example, it may be true that a particular probe hybridizes the rRNA of substantially all bacterial species despite the presence of one or a small number of mismatches between the probe and the rRNA target sequences. This illustrates how a positive result at a particular address could be "diagnostic" of a class of organisms even though the probe sequence is not necessarily present in the genomes of that class of organisms. As used herein, "diagnostic" means that a positive hybridization result can be said to indicate that a hybridizing polynucleotide is of a particular origin. Significantly, while a positive hybridization signal resulting from a precise match between a probe and a target would give a positive result at a corresponding address, the converse case is not necessarily true. More particularly, a positive hybridization result at an address does not necessarily prove that the target polynucleotide contains a sequence that is perfectly or completely complementary to the probe.

Automated devices useful for analyzing the ribosomal nucleic acids from a microorganism also will include a processor linked to the memory device. In part, the processor is used for executing an algorithm that correlates the profile of hybridization data with the identities of organisms possessing ribosomal nucleic acid sequences that could have given rise to those hybridization results. The processor also may perform a quantitative analysis to provide a basis for determining whether a numerical result from a hybridization procedure is positive or negative. While there are different approaches that can be followed to make this determination, a preferred approach takes advantage of the "part-whole" relationship among probes that are parts of the matrix. For example, a positive result would be indicated when the hybridization value is greater than a lower threshold value, and is at least several fold greater than the negative control hybridization value. Once each hybridization result has been determined to be either positive or negative, the collection of results can be assembled as a profile, a value or a "string" that can be compared with the look-up table stored in the memory device. An exemplary string of results for a four address probe matrix would be (1011) or (+/−/+/+), where "1" or "+" represent positive hybridization results and "0" or "−" represent negative hybridization results.

Commercially available spreadsheet computer software can easily be adapted for carrying out the comparison algorithm. For example, the EXCEL spreadsheet program sold by Microsoft Corp. (Redmond, Wash.) has been particularly used for creating an exemplary automated device for analyzing probe matrix hybridization results. A portion of a look-up table contained in the exemplary device had the following structure:

| Address | | | | | | | |
|---|---|---|---|---|---|---|---|
| 1 | 2 | 3 | 4 | 5 | 6 | 7 | Output |
| + | − | + | − | + | − | − | Enterococcus |
| + | − | + | − | − | + | + | Staphylococcus aureus |

-continued

| | | Address | | | | | |
|---|---|---|---|---|---|---|---|
| 1 | 2 | 3 | 4 | 5 | 6 | 7 | Output |
| + | − | + | − | − | + | − | *Staphylococcus* other than *S. aureus* ("SNA") |
| + | − | + | − | − | − | + | *Streptococcus pneumoniae* |
| + | − | + | − | − | − | − | Gram$^{(+)}$ bacteria; not the Actinomycetes subset of Gram$^{(+)}$ bacteria, not *Enterococcus*, not a member of the *Staphylococcus* genus, and not *Streptococcus pneumoniae* |

Optionally, a result delivered by the analytical device provides a list of candidate organisms corresponding to a result from the look-up table. For example, a computer algorithm for identifying candidate organisms could offer to the device operator a hyperlink for viewing a list of candidate organisms. In this example, the entry corresponding to (+/−/+/−/−/+/−/−) could be connected to a hyperlink that identifies as candidate organisms: *Enterococcus casseliflavus*, *Enterococcus durans*, *Enterococcus faecalis*, *Enterococcus faecium*, *Enterococcus gallinarum*, *Enterococcus hirae* and *Enterococcus mundtii*. This list of candidate organisms is derived from the information contained in Table 6.

Output devices that can be used with the automated analytical device include those that provide either transient or permanent outputs. Transient outputs include those that appear on visual display monitors or screens. Permanent outputs include printed records such as those produced by a printer linked to a processor. It will be apparent to those having ordinary skill in the art that each of these types of output devices can be connected to the processor so that results of the comparison between the results inputted into the processor and the look-up table stored in the memory device can be provided to the user or operator of the automated device.

Specific Examples of Probe Matrices

One version of the probe matrix has been found to be particularly useful for identifying a wide variety microorganisms, including those most often responsible for causing bacteremia or septicemia. Bacteremia is the presence of bacteria in the bloodstream as may occur for a few hours following many minor surgical operations. Septicemia is a rapid multiplication of bacteria and is marked by the presence of bacterial toxins in the blood. Septicemia is always a serious, life-threatening condition. As indicated above, typical clinical laboratory practice used for detecting and identifying organisms that cause either of these conditions involve inoculating a sterile blood culture bottle with a small quantity of patient blood to propagate microorganisms resident in the blood. The process begins with a phlebotomist thoroughly cleaning the skin area that will be punctured for drawing venous blood. This procedure may involve swabbing the area with alcohol and an iodine-containing solution. Examples of automated systems that can be used for monitoring growth of microorganisms in the blood bottles include the BACTEC 9240 (Becton Dickinson, Sparks, Md.), the BACT/ALERT (Organon Teknika, Durham, N.C.) and ESP (Difco, Detroit, Mich.). After a period of from several hours to days, bottles that produce carbon dioxide are identified by an automated monitoring system, the bottles are opened and the organisms contained in the bottle subjected to Gram-staining, standard metabolic testing for growth requirements, or the ability to breakdown certain detectable substrates. Some organisms that produce only small amounts of carbon dioxide require five days of culture before triggering a positive signal. Often, false-positive results will be obtained if contaminating skin bacteria are introduced into the blood bottle, or if the patient blood sample contains a sufficiently high number of respiring white blood cells. Previous investigations of bacteremia and septicemia concluded that only approximately 20 microorganism species account for 95% of isolates from blood bottles. Thus, it should be clear that it is unnecessary to have the capacity to determine the species of all known species of bacteria and fungi in order to produce highly useful testing apparatus that can give clinically relevant information.

Example 1 describes methods that were used to demonstrate the principle of operation that underlies the probe matrix approach for identifying microorganisms. In this Example, hybridization reactions were carried out using a collection of purified rRNAs or polynucleotide-containing lysates obtained from control microorganisms having known identities.

EXAMPLE 1

Identification of Control Microorganisms Using a Probe Matrix Hybridization

Each of seven separated hybridization vessels (either tubes or microtiter wells) received a collection of AE-labeled probes and unlabeled helper oligonucleotides, as indicated in Table 5. Each of the probes was specific for the rRNA of one species of organism or a defined grouping of organisms. In this procedure, acridinium ester-labeled probes having the sequences given in Table 5 were employed using the following addresses: (1) pan-bacterial; (2) pan-fungal; (3) Gram$^{(+)}$; (4) Actinomycetes subset of Gram$^{(+)}$; (5) the family Enterobacteriaceae and *Enterococcus* group; (6) *Staphylococcus* genus and *Campylobacter* group; and (7) species-specific probes for *E. coli*, *Staphylococcus aureus*, *Candida albicans*, *Pseudomonas aeruginosa*, and *Streptococcus pneumoniae*. Each address included about 0.1 pmol of each AE-labeled probe and about 10 pmol of each helper oligonucleotide. Either approximately 1.0-100 fmol of purified rRNA or an amount of lysate containing an equivalent amount of rRNA from cultured bacteria obtained from the American Type Culture Collection (ATCC) or from our laboratory master stock of organisms was added to the mixture of probes for each address in the matrix. After hybridizing the mixtures under high stringency conditions, label attached to unhybridized probe was inactivated and specifically hybridized probe quantitated by luminometry essentially according to the procedure given by Arnold et al., in U.S. Pat. No. 5,283,174, the disclosure of which has been incorporated by reference herein above.

The qualitative results presented in Table 6 show how a large number of different microbes can be typed using a single probe matrix. Addresses that gave quantitative hybridization signals at least 2 fold greater than background signals detected in negative control reactions were judged as representing positive hybridization results. Shaded entries in Table 6 represent positive hybridization results at the indicated addresses.

TABLE 6

Qualitative Hybridization Results

| Organism | GP #* | Pan-Bacterial Probe | Pan-Fungal Probe | Gram(+) Probe | Actinomycetes Probe | Enteric & Enterococcus | Staph & Camplyobacter | Species Probes |
|---|---|---|---|---|---|---|---|---|
| Bacillus brevis | 1180 | ■ | | ■ | | | | |
| Bacillus subtilis | 20 | ■ | | | | | | |
| Bacteroides fragilis | 227 | ■ | | | | | | |
| Candida albicans | PN 102395 | | ■ | | | | | ■ |
| Candida glabrata | 1123 | | ■ | | | | | |
| Candida parapsilosis | 1085 | | ■ | | | | | |
| Citrobacter diversus | 845 | ■ | | | | ■ | | |
| Citrobacter freundii | 408 | ■ | | | | | | |
| Corynebacterium aquaticum | 599 | ■ | | | ■ | | | |
| Corynebacterium xerosis | 552 | ■ | | | ■ | | | |
| Enterobacter aerogenes | 722 | ■ | | | | ■ | | |
| Enterobacter agglomerans | 723 | ■ | | | | ■ | | |
| Enterobacter cloacae | 367 | ■ | | | | ■ | | |
| Enterobacter gergoviae | 724 | ■ | | | | ■ | | |
| Enterobacter sakazaki | 157 | ■ | | | | | | |
| Enterococcus avium | 1174 | ■ | | ■ | | ■ | | |
| Enterococcus casseliflavus | 999 | ■ | | ■ | | ■ | | |
| Enterococcus cecorum | 1400 | ■ | | ■ | | ■ | | |
| Enterococcus dispar | 1398 | ■ | | ■ | | ■ | | |
| Enterococcus durans | 888 | ■ | | ■ | | ■ | | |
| Enterococcus faecalis | 1013 | ■ | | ■ | | ■ | | |
| Enterococcus faecium | 1027 | ■ | | ■ | | ■ | | |
| Enterococcus gallinarum | 1000 | ■ | | ■ | | ■ | | |
| Enterococcus hirae | 1001 | ■ | | ■ | | ■ | | |
| Enterococcus mundtii | 998 | ■ | | ■ | | ■ | | |
| Escherichia coli | 88 | ■ | | | | ■ | | ■ |
| Klebsiella oxytoca | 727 | ■ | | | | ■ | | |
| Klebsiella ozaenae | 728 | ■ | | | | ■ | | |
| Klebsiella pneumoniae | 40 | ■ | | | | ■ | | |

TABLE 6-continued

Qualitative Hybridization Results

| Organism | GP #* | Pan-Bacterial Probe | Pan-Fungal Probe | Gram(+) Probe | Actinomycetes Probe | Enteric & Enterococcus | Staph & Camplyobacter | Species Probes |
|---|---|---|---|---|---|---|---|---|
| Klebsiella rhinoscleromatis | 242 | ■ | | | | | | |
| Lactobacillus acidophilus | 818 | | | ■ | | | | |
| Lactobacillus jensenii | 1018 | | | ■ | | | | |
| Listeria grayi | 851 | ■ | | ■ | | | | |
| Listeria ivanovii | 847 | ■ | | ■ | | | | |
| Listeria monocytogenes | 803 | ■ | | ■ | | | | |
| Listeria seeligeri | 895 | ■ | | ■ | | | | |
| Listeria welshimeri | 1402 | ■ | | ■ | | | | |
| Micrococcus luteus | 419 | ■ | | ■ | | | | |
| Mycobacteria tuberculosis | PN 101397 | ■ | | ■ | ■ | | | |
| Proteus mirabilis | 179 | ■ | | | | ■ | | |
| Proteus vulgaris | 181 | ■ | | | | ■ | | |
| Pseudomonas aeruginosa | 736 | ■ | | | | | | ■ |
| Pseudomonas cepacia | 204 | ■ | | | | | | |
| Pseudomonoa maltophilia | 207 | ■ | | | | | | |
| Salmonella typhimurium | 166 | ■ | | | | ■ | | |
| Serratia liquifaciens | 170 | ■ | | | | | | |
| Staphylococcus aureus | 1397 | ■ | | ■ | | | ■ | ■ |
| Staphylococcus delphini | 1334 | ■ | | ■ | | | ■ | |
| Staphylococcus epidermidis | 742 | ■ | | ■ | | | ■ | |
| Staphuylococcus haemolyticus | 1221 | ■ | | ■ | | | ■ | |
| Staphylococcus homoninis | 1222 | ■ | | ■ | | | ■ | |
| Staphyulococcus hyicus-hyicus | 1347 | ■ | | ■ | | | ■ | |
| Staphylococcus intermedius | 1223 | ■ | | ■ | | | ■ | |
| Staphylococcus saprophyticus | 743 | ■ | | ■ | | | ■ | |
| Staphyulococcus simulans | 1225 | ■ | | ■ | | | ■ | |

TABLE 6-continued

Qualitative Hybridization Results

| Organism | GP #* | Pan-Bacterial Probe | Pan-Fungal Probe | Gram(+) Probe | Actinomycetes Probe | Enteric & Enterococcus | Staph & Camplyobacter | Species Probes |
|---|---|---|---|---|---|---|---|---|
| Staphylococcus warneri | 1226 | ■ | | ■ | | | ■ | |
| Streptococcus agalactiae | 744 | ■ | | ■ | | | | |
| Streptococcus anginosus | 1315 | ■ | | ■ | | | | |
| Streptococcus avium | 745 | ■ | | ■ | | | | |
| Streptococcus bovis | 922 | ■ | | ■ | | | | |
| Streptococcus dysgalactiae | 249 | ■ | | ■ | | | | |
| Streptococcus equi | 1386 | ■ | | ■ | | | | |
| Streptococcus equinus | 920 | ■ | | ■ | | | | |
| Streptococcus equisimilis | 1349 | ■ | | ■ | | | | |
| Streptococcus grp G | 1194 | ■ | | ■ | | | | |
| Streptococcus grp. C | 1195 | ■ | | ■ | | | | |
| Streptococcus mutans | 1014 | ■ | | ■ | | | | |
| Streptococcus pneumoniae | 1172 | ■ | | ■ | | | | ■ |
| Streptococcus pyogenes | 1170 | ■ | | ■ | | | | |
| Streptococcus salivarius | 816 | ■ | | ■ | | | | |
| Streptococcus sanguis | 1206 | ■ | | ■ | | | | |
| Streptococcus sp group F2 | 1193 | ■ | | ■ | | | | |
| Streptococcus sp group B type III | 1012 | ■ | | ■ | | | | |
| Streptococcus uberis | 250 | ■ | | ■ | | | | |

*GP# identifies organisms by master log numbers for Gen-Probe Incorporated.

The results presented in Table 6 confirmed that the hybridization procedure gave the expected pattern of results at each of the seven addresses in the matrix. For example, rRNA from S. aureus gave a positive hybridization signal at the pan-bacterial address and a negative hybridization signal at the pan-fungal address of the matrix. This confirmed the absence of any fungally derived rRNA in the S. aureus rRNA sample, as expected. The positive signal at the Gram$^{(+)}$ address was consistent with the fact that S. aureus is a Gram$^{(+)}$ bacterium. The negative results at addresses corresponding to the Actinomycetes subset of Gram$^{(+)}$ bacteria and the family Enterobacteriaceae and Enterococcus group confirmed that S. aureus was not among the bacteria classified as Actinomycetes, or among the Enteric or Enterococcus groups of bacteria. Since S. aureus is a member of the Staphylococcus genus, even though it is not a member of the Campylobacter group, a positive hybridization result at the sixth address corresponding to these probes was appropriate. This latter result exemplifies how a positive hybridization with any one of a plurality of probes at a particular address will givte signal. Finally, the positive hybridization signal at the seventh address corresponding to a collection of species-specific probes was appropriate because this locus included a species-specific probe for S. aureus.

Importantly, if the positive hybridization result at the address corresponding to the five species-specific probes had been taken in isolation from the other results in the matrix, only an ambiguous interpretation of the data would have been possible. More particularly, the result would have indicated that the hybridizing rRNA(s) were from at least one of the species given by E. coli, S. aureus, C. albicans, P. aeruginosa and S. pneumoniae. However, when viewed in the context of other results in the hybridization matrix, it becomes clear that certain of these species were ruled out by other results in the matrix. For example, the negative result at the address corresponding to the pan-fungal probe meant that the hybridizing rRNA could not have been from the yeast, *C. albicans*. Similarly, the negative hybridization result at the address corresponding to the Enteric bacteria and *Enterococcus* meant that the hybridizing rRNA at the species-specific address could not have been from *E. coli*, which is an Enteric bacterium. The positive hybridization results at the address corresponding to *Staphylococcus* and *Campylobacter* group probes at the sixth address in the matrix meant that the positive hybridization result at the species-specific address could not have been due to either *P. aeruginosa* or *S. pneumoniae* because these organisms would have given negative hybridization results at the address corresponding to the *Staphylococcus* genus and *Campylobacter* group. This illustrates how the rRNA from an organism gives a distinctive pattern of hybridization results using the above-described probe matrix approach.

Importantly, Table 6 also represents a look-up table that can be used for decoding the identity of an organism characterized by one of the qualitative hybridization profiles in the Table. For example, upon consulting Table 6 it should be clear that a profile given by "(+/−/+/−/−/+/+)," corresponding to positive and negative hybridization results at the seven addresses in the Table, would identify a microorganism as *Staphylococcus aureus*.

During the development of the invention it was unexpectedly discovered that the matrix-based method of identifying microorganisms also can resolve the identities of microorganisms contained in a mixed sample of microorganisms. More particularly, it was discovered that even seemingly well-isolated colonies grown on nutrient agar plates in microbiology laboratories occasionally contained more than one species of microorganism. This capacity for detecting the presence of more than one organism, and the ability to determine the identities of those organisms without further isolation or purification steps, strongly evidences the advantages of the invention over alternative molecular diagnostic techniques. For example, polynucleotide sequencing of a mixture of templates representing rRNA or rDNA from different organisms would give ambiguous results that could not reliably be sorted into independent sequences. Similarly, probe-based methods of identifying microorganisms using less comprehensive hybridization strategies, including strategies that derive no confirming results from negative hybridization signals can overlook the presence of a second organism if a positive hybridization result is achieved with a first species-specific probe. Thus, the method disclosed herein can be used to carry out analyses that could not otherwise be performed by alternative approaches.

The quantitative nature of the results obtainable in the matrix-based method of microbe identification, together with the ability to draw inferences from negative hybridization results wherein a probe fails to hybridize a target polynucleotide is the basis underlying this unique attribute of the invention. Indeed, normalizing the results of a matrix hybridization procedure to the signal measured at a pan-bacterial or a pan-fungal address can render the system sufficiently quantitative that some mixtures of microorganisms can be resolved in a single hybridization procedure.

Example 2 describes the procedures that demonstrated the matrix-based method of microbe identification could detect and resolve mixtures of microorganisms.

EXAMPLE 2

Resolution of Mixed Cultures of Microorganisms

Several control bacterial rRNA samples were tested using a seven-address probe matrix as described under Example 1. Lysates containing rRNAs from three different strains of the *Streptococcus pyogenes* (strains A-C) were tested in the probe matrix. The hybridization and quantitation procedures disclosed by Arnold et al., in U.S. Pat. No. 5,283,174 were employed to quantitate target rRNAs bound by the probes at the various addresses. A fourth strain (strain D) of the same species of bacterium also was tested according to the same procedures.

Table 7 presents normalized quantitative results indicating the hybridization signals at each of the addresses in the probe matrix. The average Relative Light Unit (RLU) readings for *S. pyogenes* strains A-C at each of the seven addresses appear in the first row of the Table. Results obtained for *S. pyogenes* strain D appear in the second row of the Table. All values are normalized to the readings obtained at the respective pan-bacterial addresses. In this instance, normalized values greater than 20% of the pan-bacterial signal were considered positive.

TABLE 7

Resolution of a Mixed Bacterial Culture by Probe Matrix Analysis*

| Sample | pan-bacterial | pan-fungal | Gram(+) | High (G + C) | Enteric; *Enterococcus* | *Staph* genus; *Campylobacter* | Species address |
| --- | --- | --- | --- | --- | --- | --- | --- |
| *Strep. pyogenes* strains A-C (Avg, n = 3) | 100 | 0.5 | 31 | 1.0 | 1.3 | 0.8 | 2.5 |
| *Strep. pyogenes* Strain D | 100 | 0.5 | 51 | 0.8 | 1.5 | 29 | 2.3 |

*Numerical values have been normalized to the hybridization signal observed at the pan-bacterial address and are presented as percentages (%).

As indicated in Table 7, the normalized averages for three different strains of *S. pyogenes* (strains A-C) gave a profile showing positive hybridization results at the pan-bacterial and Gram$^{(+)}$ addresses. In comparison, the fourth strain of the species (strain D) gave a profile showing positive hybridization results at the pan-bacterial, Gram$^{(+)}$ and *Staphylococcus* genus/*Campylobacter* group addresses, with a slightly increased relative signal at the Gram$^{(+)}$ address when compared with the average of the other strains. Since *S. pyogenes* is a Gram$^{(+)}$ bacterium that is not a member of the *Staphylococcus* genus or the *Campylobacter* group, it was clear that the positive hybridization signal observed at the *Staphylococcus* genus/*Campylobacter* address must have been due to the presence of hybridizing rRNA from a contaminating bacterium other than *S. pyogenes*. Since *Campylobacter* bacteria are Gram$^{(−)}$, since Staphylococcal bacteria are Gram$^{(+)}$, and in view of the observation that the relative signal at the Gram$^{(+)}$ address was increased and not decreased, it follows that Gram$^{(+)}$ *Staphylococcus* must have been present as a contaminant in the starting sample of bacteria that was used to prepare the rRNA for hybridization. Since the species-specific *S. aureus* probe present at the species address in the matrix failed to give a positive hybridization signal, it follows that the contaminating bacterium must have been a *Staphylococcus* bacterium other than *S. aureus*, or "SNA." This illustrates how the matrix-based method of identifying microbes can resolve mixtures of microorganisms. Numerous other examples of mixed populations of microbes also have been resolved using this technique.

As indicated above, in at least some cases the matrix-based method of microbe identification advantageously can be used to resolve the identities of organisms that are present in mixed populations. To demonstrate the quantitative aspect of the procedure, an experiment was conducted to compare: (a) actual hybridization results obtained using mixtures of control lysates, and (b) quantitative values predicted for the hybridization based on results obtained using isolated controls. In the first part of the experiment, known amounts of lysates from three bacterial species were combined and hybridized according to a standard probe matrix hybridization procedure. In the second half of the procedure mixtures of the rRNA-containing lysates were prepared and subjected to the same hybridization procedure. The results obtained for these mixed samples were compared with the values that would have been expected based on the proportional contributions of each component in the mixture to illustrate how mixed samples can be resolved quantitatively. Although the following illustrative procedure employed mixtures of lysates that had been separately prepared from cultured microorganisms, it should be understood that lysates prepared from mixed cultures of microorganisms would give similar results.

Example 3 describes the procedure that demonstrated nucleic acid samples from two different microorganisms could be quantitatively resolved using a probe matrix hybridization protocol.

EXAMPLE 3

Resolving Mixed Populations of Microorganisms Using a Polynucleotide Probe Matrix Three different rRNA-containing bacterial lysates were prepared and subjected to the probe matrix hybridization and detection procedure described in Example 1. *Enterococcus faecalis* (ATCC# 29212; a Gram$^{(+)}$ *Enterococcus*), *Streptococcus uberis* (ATCC# 27958; a Gram$^{(+)}$ bacterium) and *E. coli* (ATCC# 10798; a Gram$^{(-)}$ member of the Enterobacteriaceae) were used as sources of rRNA in these procedures. A mixture of rRNAs purified from *E. coli, C. albicans, S. aureus* and *M. chelonae* served as a positive hybridization control while hybridization buffer served as a negative control. The volume of rRNA-containing lysate used in the 100 μl hybridization reactions was held constant at 50 μl. Table 8 presents the quantitative hybridization results that were obtained using each of the three bacterial lysates in isolation.

TABLE 8

Probe Matrix Hybridization Using Bacterial Lysate Controls (in RLU)

| Address | Positive Control | Negative Control | S. uberis | E. coli | E. faecalis |
|---|---|---|---|---|---|
| pan-bacterial | 152480 | 603 | 86520 | 35860 | 79210 |
| pan-fungal | 44200 | 760 | 628 | 603 | 595 |
| Gram$^{(+)}$ | 90390 | 873 | 47270 | 818 | 44730 |
| High(G + C) | 90680 | 1173 | 1020 | 1132 | 1038 |
| Enteric/ Enterococcus | 31560 | 2113 | 1810 | 29040 | 37600 |
| Staph genus/ Campylobacter | 26060 | 883 | 822 | 817 | 803 |
| Species Probes | 100790 | 2116 | 1854 | 32390 | 1784 |

Hybridization and detection procedures also were conducted using lysates of *Enterococcus faecalis* and *Streptococcus uberis* that had been combined in volume ratios of 4:1, 1:1 and 1:4. Lysates of *E. coli* and *Streptococcus uberis* similarly were combined in ratios of 1:1 and 1:4 and then used in the hybridization procedure. Results obtained using these mixed samples are presented in Table 9.

TABLE 9

Hybridization Results (in RLU) for Bacterial Lysates Combined in Varying Proportions

| Address | Ef/Su (4:1) | Ef/Su (1:1) | Ef/Su (1:4) | Ec/Su (4:1) | Ec/Su (1:1) | Ec/Su (1:4) |
|---|---|---|---|---|---|---|
| pan-bacterial | 84500 | 88730 | 85000 | 47710 | 60500 | 72950 |
| pan-fungal | 715 | 675 | 647 | 637 | 669 | 624 |
| Gram$^{(+)}$ | 48960 | 45850 | 46480 | 9064 | 23350 | 37440 |
| High(G + C) | 1120 | 1094 | 1162 | 1013 | 1027 | 1028 |
| Enteric/ Enterococcus | 34070 | 23080 | 10542 | 24130 | 17030 | 8066 |
| Staph genus/ Campylobacter | 900 | 860 | 783 | 850 | 812 | 817 |
| Species Probes | 2470 | 2414 | 2005 | 26610 | 17410 | 8433 |

Ec is *E. coli*
Ef is *Enterococcus faecalis*
Su is *Streptococcus uberis*

Finally, the measured RLU values presented in Table 9 were compared with values that were expected based on proportionate combinations of the numerical results presented in Table 8. The results of this latter comparison are presented as percentages in Table 10.

TABLE 10

Predicted Hybridization Results as Percentages of Measured Values

| Address | Ef/Su (4:1) | Ef/Su (1:1) | Ef/Su (1:4) | Ec/Su (4:1) | Ec/Su (1:1) | Ec/Su (1:4) |
|---|---|---|---|---|---|---|
| pan-bacterial | 95 | 93 | 100 | 96 | 101 | 105 |
| pan-fungal | na | na | na | na | na | na |
| Gram$^{(+)}$ | 92 | 100 | 101 | 112 | 103 | 101 |
| High(G + C) | na | na | na | na | na | na |
| Enteric/ Enterococcus | 89 | 85 | 85 | 98 | 91 | 90 |
| Staph genus/ Campylobacter | na | na | na | na | na | na |
| Species Probes | na | na | na | 99 | 98 | 94 |

Ec is *E. coli*
Ef is *Enterococcus faecalis*
Su is *Streptococcus uberis*
na is "not applicable"

The results shown in Table 10 demonstrate that the calculated values and the actual values for probe hybridization in the matrix-based procedure corresponded closely. Indeed, the actual and predicted values for the hybridization differed from each other by no more than about 15%. This proved that the probe matrix based hybridization procedure could be used to derive quantitative hybridization data that reflected the relative contributions of rRNA from different microorganism species contained in the mixture. Thus, the matrix-based hybridization protocol can be used for determining the relative contributions of different microorganisms in mixed populations of microorganisms.

The following Example describes how the matrix-based method of microbe identification can be used to diagnose septicemia.

EXAMPLE 4

Diagnosis of Septicemia Using Matrix-Based Microbe Identification

A human patient suspected of having an infection of the bloodstream is first identified by a physician. A venous blood sample is drawn from the patient at a site on the skin that has been cleansed with alcohol and an iodine solution according to standard medical procedures. The sample is used to innoculate a blood culture bottle which is then held at 37° C. and monitored for $CO_2$ production in an automated incubator. After two days the culture appears turbid and is judged by visual inspection to contain gas-producing microorganisms. A liquid sample removed from the culture bottle is subjected to selective centrifugation steps (Davis et al., *J. Clin Microbiol.* 29:2193 (1991)) to collect microorganisms. First, a 1.5 ml sample of broth from the bottle is removed and centrifuged for 2 seconds at approximately 9,600×g to sediment red blood cells. The supernatant is isolated and subjected to centrifugation at 9,600×g for 1 minute to concentrate microbes. The resulting pellet is lysed by standard laboratory procedures and the released polynucleotides subjected to matrix-based hybridization analysis using the seven-address probe matrix described under Example 1. Positive hybridization signals are detected only at the pan-fungal address and the address corresponding to species-specific probes for *E. coli, S. aureus, C. albicans, P. aeruginosa* and *S. pneumoniae*. Based on these results, it is concluded that the patient's blood harbors *Candida albicans*. Appropriate antifungal therapy is initiated immediately and the patient's condition improves.

As described herein, the matrix-based method of microbe identification clearly can provide a species-level identification of microorganisms with the accuracy of an amplification and sequencing protocol, but with the convenience and simplicity of a probe hybridization approach. However, the matrix-based method of identifying microbes also provides the added ability to resolve the identities of microbes that are contained in mixed cultures of microorganisms. Moreover, the matrix-based method of microbe identification also extracts meaningful information from negative hybridization results, a feature that is not integral to other molecular diagnostic procedures.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A device for detecting nucleic acids, comprising:
a solid support; and
a plurality of addresses disposed on the solid support, each address comprising at least one detectably labeled probe capable of hybridizing to ribosomal nucleic acids from at least one microbial species under high stringency conditions, said plurality of addresses comprising
a first address comprising one or more detectably labeled probes capable of hybridizing to ribosomal nucleic acids of more than one microbial species, and
a second address comprising a mixture of
(a) a first detectably labeled probe capable of hybridizing to ribosomal nucleic acids from a subset of species having ribosomal nucleic acids that hybridize at the first address, and
(b) a second detectably labeled probe capable of hybridizing to ribosomal nucleic acids from a microbial species which does not have ribosomal nucleic acids that hybridize at the first address, but not capable of hybridizing to ribosomal nucleic acids from any microbial species having ribosomal nucleic acids that hybridize at the first address.

2. The device of claim 1, wherein said subset of species having ribosomal nucleic acids that hybridize at the first address comprises at least one bacterial species having ribosomal nucleic acids that hybridize at the first address.

3. The device of claim 2, wherein said microbial species which does not have ribosomal nucleic acids that hybridize at the first address comprises a bacterial species which does not have ribosomal nucleic acids that hybridize at the first address.

4. The device of claim 2, wherein said microbial species which does not have ribosomal nucleic acids that hybridize at the first address comprises a fungal species which does not have ribosomal nucleic acids that hybridize at the first address.

5. The device of claim 1, wherein said subset of species having ribosomal nucleic acids that hybridize at the first address comprises at least one fungal species having ribosomal nucleic acids that hybridize at the first address.

6. The device of claim 5, wherein said microbial species which does not have ribosomal nucleic acids that hybridize at the first address comprises a bacterial species which does not have ribosomal nucleic acids that hybridize at the first address.

7. The device of claim 5, wherein said microbial species which does not have ribosomal nucleic acids that hybridize at the first address comprises a fungal species which does not have ribosomal nucleic acids that hybridize at the first address.

8. The device of claim 1, wherein each of said at least one detectably labeled probe capable of hybridizing to ribosomal nucleic acids is a detectably labeled soluble probe capable of hybridizing to ribosomal nucleic acids.

9. The device of claim 8, wherein each of said at least one detectably labeled soluble probe capable of hybridizing to ribosomal nucleic acids comprises a label selected from the group consisting of a chemiluminescent label, a redox-active electron transfer label, and a fluorescent label.

10. The device of claim 9, wherein each of said at least one detectably labeled soluble probe capable of hybridizing to ribosomal nucleic acids comprises a chemiluminescent label.

11. The device of claim 1, wherein said first address is selected from the group consisting of:
(a) a pan-bacterial address that hybridizes to ribosomal nucleic acids from a plurality of species of Gram(+) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*,
(b) a pan-fungal address that hybridizes to ribosomal nucleic acids from a plurality of fungal species,
(c) a Gram(+) address that hybridizes to ribosomal nucleic acids of a plurality of Gram(+) bacteria, wherein said plurality of Gram(+) bacteria comprise a plurality of bacteria in the genus *Staphylococcus*,
(d) a family Enterobacteriaceae address that hybridizes to ribosomal nucleic acids from a plurality of bacteria in the family Enterobacteriaceae, and
(e) a *Staphylococcus* genus address that hybridizes to ribosomal nucleic acids from a plurality of species in the *Staphylococcus* genus.

12. The device of claim 2, wherein said at least one bacterial species having ribosomal nucleic acids that hybridize at the first address comprises a species selected from the group consisting of *Escherichia coli, Staphylococcus aureus, Pseudomonas aeruginosa,* and *Streptococcus pneumoniae.*

13. The device of claim 12, wherein said first address is a family Enterobacteriaceae address that specifically hybridizes ribosomal nucleic acids from a plurality of bacteria in the family Enterobacteriaceae, and wherein said at least one bacterial species having ribosomal nucleic acids that hybridize at the first address comprises *Escherichia coli.*

14. The device of claim 2, wherein said first address is a Gram(+) address that specifically hybridizes ribosomal nucleic acids of a plurality of Gram(+) bacteria, and wherein said microbial species which does not have ribosomal nucleic acids that hybridize at the first address comprises *Escherichia coli.*

15. The device of claim 3, wherein said first address is a *Staphylococcus* genus address that hybridizes ribosomal nucleic acids from a plurality of species in the *Staphylococcus* genus.

16. The device of claim 15, wherein said at least one bacterial species having ribosomal nucleic acids that hybridize at the first address comprises *Staphylococcus aureus.*

17. The device of claim 4, wherein said fungal species which does not have ribosomal nucleic acids that hybridize at the first address comprises *Candida albicans.*

18. The device of claim 5, wherein said at least one fungal species having ribosomal nucleic acids that hybridize at the first address comprises *Candida albicans.*

19. The device of claim 6, wherein said bacterial species which does not have ribosomal nucleic acids that hybridize at the first address comprises a species selected from the group consisting of *Escherichia coli, Staphylococcus aureus, Pseudomonas aeruginosa,* and *Streptococcus pneumoniae.*

20. The device of claim 7, wherein said first detectably labeled probe is capable of hybridizing to ribosomal nucleic acids from *Candida albicans* but not to the ribosomal nucleic acids of other species in the genus *Candida.*

* * * * *